US007541035B2

(12) United States Patent
Berzofsky et al.

(10) Patent No.: US 7,541,035 B2
(45) Date of Patent: Jun. 2, 2009

(54) IMMUNOGENIC PEPTIDES FOR THE TREATMENT OF PROSTATE AND BREAST CANCER

(75) Inventors: Jay A. Berzofsky, Bethesda, MD (US); SangKon Oh, Bethesda, MD (US); Ira Pastan, Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 274 days.

(21) Appl. No.: 10/559,329

(22) PCT Filed: Jun. 2, 2004

(86) PCT No.: PCT/US2004/017574

§ 371 (c)(1),
(2), (4) Date: Dec. 2, 2005

(87) PCT Pub. No.: WO2005/000889

PCT Pub. Date: Jan. 6, 2005

(65) Prior Publication Data

US 2006/0140967 A1    Jun. 29, 2006

Related U.S. Application Data

(60) Provisional application No. 60/476,467, filed on Jun. 5, 2003.

(51) Int. Cl.
C07K 5/00 (2006.01)
(52) U.S. Cl. ............... 424/185.1; 530/300; 530/350; 435/7.1; 435/7.8; 435/34; 435/320.1; 435/325; 536/23.5; 436/501; 424/277.1
(58) Field of Classification Search .......... 530/2, 530/328, 350, 300; 536/23.5; 435/320.1, 435/325, 7.1, 7.8, 34; 424/185.1, 277.1; 436/501; 514/2
See application file for complete search history.

(56) References Cited

U.S. PATENT DOCUMENTS

| 5,763,219 | A | * | 6/1998 | Keyomarsi | ............... 435/69.1 |
| 6,326,471 | B1 | | 12/2001 | Kokolus et al. | |
| 6,387,888 | B1 | | 5/2002 | Mincheff et al. | |
| 6,500,641 | B1 | | 12/2002 | Chen et al. | |
| 2001/0053519 | A1 | * | 12/2001 | Fodor et al. | ............... 435/6 |

FOREIGN PATENT DOCUMENTS

| WO | WO 99/61068 | 12/1999 |
| WO | WO 01/04309 | 1/2001 |
| WO | WO 02/077012 | 10/2002 |
| WO | WO 03/009814 | 2/2003 |

OTHER PUBLICATIONS

Holmes (Expert Opinion on Investigational Drugs. 2001; 10: 511-519).*
Daniel et al. (Virology. 1994 202: 540-549).*
Schirle et al. (J. Immunol. Methods. 2001; 257: 1-16).*
Fisk et al. (J. Immunother. Emphasis Tumor Immunol. Nov. 1995; 18 (4): 197-209).*
Huard et al. (Int. Immunol. 1997; 9 (11): 1701-1707).*
Ruppert et al. (Cell. Sep. 10, 1993; 74 (5): 929-937).*
Valmori et al. (J. Immunol. 1998; 161: 6956-6962).*
Guichard et al. (J. Med. Chem. 2000; 43: 3803-3808).*
Andersen et al. (Tissue Antigens. Jun. 2000; 55 (6): 519-531).*
Feltkamp et al. (Mol. Immunol. Dec. 1994; 31 (18): 1391-1401).*
van der Burg et al. (J. Immunol. May 1, 1996; 156 (9): 3308-3314).*
Valmori et al. (Journal of Immunology. 1998; 160: 1750-1758).*
Verma et al. (Nature 1997, 389: 239-242).*
Amalfitano et al. (Current Gene Therapy 2002, 2: 111-133).*
Pandha et al. (Current Opinion in Investigational Drugs 2000; 1 (1): 122-134).*
Saijo et al. (Cancer Sci. Oct. 2004; 95 (10): 772-776).*
Kelland (Eur. J. Cancer. Apr. 2004; 40 (6): 827-836).*
Bergers et al. (Current Opinion in Genetics and Development. 2000; 10: 120-127).*
Wang et al. (Exp. Opin. Biol. Ther. 2001; 1 (2): 277-290).*
Bins et al. (J. Immunother. Feb.-Mar. 2007; 30 (2): 234-239).*
Cox et al. (Science. 1994; 264: 716-719).*
Arceci (Journal of Molecular Medicine. 1998; 76: 80-93).*
Lee et al. (Journal of Immunology. 1999; 163: 6292-6300).*
Zaks et al. (Cancer Research. 1998; 58: 4902-4908).*
Gao et al. (Journal of Immunotherapy 2000; 23: 643-653).*
Hu et al. (Cancer Research. 1996; 56: 2479-2483).*
Jaeger et al. (International Journal of Cancer. 1996; 66: 162-169).*
Mukherji et al. (Proceedings of the National Academy of Science USA. 1995; 92: 8078-8082).*
Bocchia et al. (Haematologica. 2000; 85; 1172-1206).*
Altuvia et al., "A Structure-Based Algorithm to Predict Potential Binding Peptides to MHC Molecules with Hydrophobic Binding Pockets," *Human Immunol.* 58:1-11 (1997).
Bodey et al., "Failure of Cancer Vaccines: The Significant Limitations of this Approach to Immunotherapy," *Anticancer Research* 20:2665-2676 (2000).

(Continued)

*Primary Examiner*—Stephen L Rawlings
(74) *Attorney, Agent, or Firm*—Klarquist Sparkman, LLP

(57) ABSTRACT

Immunogenic T-cell receptor gamma Alternate Reading Frame Protein (TARP) polypeptides are disclosed herein. These immunogenic TARP polypeptides include nine consecutive amino acids of the amino acid sequence set forth as SEQ ID NO: 9 and do not comprise amino acids 1-26 or amino acids 38-58 of SEQ ID NO: 1. Several specific, non-limiting examples of these polypeptides are set forth as SEQ ID NOs: 3-7. Nucleic acids encoding these polypeptides, and host cells transfected with these nucleic acids, are also disclosed. Methods of using these polypeptides, and polynucleotides encoding these polypeptides, for the treatment of breast and prostate cancer are also disclosed.

25 Claims, 8 Drawing Sheets

OTHER PUBLICATIONS

Boon et al., "Toward a Genetic Analysis of Tumor Rejection Antigens," *Advances in Cancer Research* 58:177-211 (1999).

Bowie et al., "Deciphering the Message in Protein Sequences: Tolerence to Amino Acid Substitutions," *Science* 247:1306-1310 (1990).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *J. Cell Biology* 111:2129-2138 (1990).

Carlsson et al., "Generation of Cytotoxic T Lymphocytes Specific for the Prostate and Breast Tissue Antigen TARP," *The Prostate* 61:161-170 (2004).

Cheng et al., "Characterization of the Androgen-Regulated Prostate-Specific T Cell Receptor γ-Chain Alternate Reading Frame Protein (TARP) Promoter," *Endocrinology* 144(8):3433-3440 (2003).

Corman et al., "Recognition of prostate-specific antigenic peptide determinants by human CD4 and CD8 cells," *Clin Exp Immunol.* 114(2):166-172 (1998) (*Abstract Only*).

Correale et al., "In Vitro Generation of Human Cytotoxic T Lymphocytes Specific for Peptides Derived from Prostate-Specific Antigen," *J. Natl. Cancer Institute* 89(4):293-300 (1997).

Critchfield et al., "The Future of DNA Diagnostics," *Disease Markers* 15:108-111 (1999).

Davodeau et al., "Secretion of Disulfide-linked Human T-cell Receptor γδ Heterodimers," *The Journal of Biological Chemistry*, 268(21):15455-15460 (1993).

Denkberg et al., "Modification of a tumor-derived peptide at an HLA-A2 anchor residue can alter the conformation of the MHC-peptide complex: probing with TCR-like recombinant antibodies," *J. Immunol.* 169(8):4399-4407 (2002) (Abstract Only).

Essand et al., "High expression of a specific T-cell receptor γ transcript in epithelial cells of the prostate," *Proc. Natl. Acad. Sci. USA*, 96:9287-9292 (1999).

Ezzell, "Cancer 'Vaccines': An Idea Whose Time Has Come?" *J. NIH Research* 7:46-49 (1995).

Greenspan et al., "Defining epitopes: It's not as easy as it seems," *Nature Biotechnology* 17:936-937 (1999).

Greten et al., "Peptide-β2-microglobulin-MHC fusion molecules bind antigen-specific T cells and can be used for multivalent MHC-Ig complexes," *J. Immunol. Methods* 271(1-2):125-135 (2002) (Abstract Only).

Guichard et al., "Melanoma Peptide MART-1(27-35) Analogues with Enhanced Binding Capacity to the Human Class I Histocompatibility Molecule HLA-A2 by Introduction of a β-Amino Acid Residue: Implications for Recognition by Tumor-Infiltrating Lymphocytes," *J. Med. Chem.* 43:3803-3808 (2000).

Gura, "Systems for Identifying New Drugs are Often Faulty," *Science* 278:1041-1042 (1997).

Hawkins et al., "PEDB: the Prostate Expression Database," *Nucleic Acids Research*, 27(1):204-208 (1999).

Heiser et al., "Introduction of Polyclonal Prostate Cancer-Specific CTL Using Dendritic Cells Transfected with Amplfied Tumor RNA," *J. Immunol.* 166:2953-2960 (2001).

Huang et al., "Prostate cancer expression profiling by cDNA sequencing analysis," *Genomics*, 59(2):178-186 (1999) (EMEST Database Entry AI557112, Accession No. AI557112).

Johansen et al., "Peptide binding to MHC class I is determined by individual pockets in the binding groove," *Scand J. Immunol.* 46(2):137-146 (1997) (Abstract Only).

Kondo et al., "Prominent Roles of Secondary Anchor Residues in Peptide Binding to HLA-A24 Human Class I Molecules," 155:4307-4312 (1995).

Lazar et al., "Transforming Growth Factor α: Mutation of Aspartic Acid 47 and Leucine 48 Results in Different Biological Activities," *Molecular and Cellular Biology* 8(3):1247-1252 (1988).

Lim et al., "Selection of Peptides that Bind to the HLA-A2.1 Molecule by Molecular Modelling," *Molecular Immunol.* 33(2):221-230 (1996).

Lu et al., "Recognition of Prostate Tumor Cells by Cytotoxic T Lymphocytes Specific for Prostate-specific Membrane Antigen," *Cancer Research* 62:5807-5812 (2002).

Maeda et al., "The T Cell Receptor γ-Chain Alternate Reading Frame Protein (TARP), a Prostate-specific Protein Localized in Mitochondria," *J. Biol. Chemistry* 279(3):24561-24568 (2004).

Nussbaum, et al., "Using the World Wide Web for predicting CTL epitopes," *Current Opinion in Immunology* 15:69-74 (2003).

Oh, et al., "Human CTLs to Wild-Type and Enhanced Epitopes of a Novel Prostate and Breast Tumor-Associated Protein, TARP, Lyse Human Breast Cancer Cells," *Cancer Research* 64:2610-2618 (Apr. 1, 2004).

Ruppert et al., "Prominent Role of Secondary Anchor Residues in Peptide Binding to HLA-A2.1 Molecules," *Cell Press* 137:929-937 (1993).

Sarobe et al., "Enhanced In Vitro Potency and In Vivo Immunogenicity of a CTL Epitope from Hepatitis C Virus Core Protein following Amino Acid Replacement at Secondary HLA-A2.1 Binding Positions," *J. Clin. Invest.* 102(6):1239-1248 (Sep. 1998).

Schonbach et al., "Fine tuning of peptide binding to HLA-B*3501 molecules by nonanchor residues," *J. Immunol.* 154(11):5951-5958 (1995) (Abstract Only).

Sharma et al., "Class I Major Histocompatibility Complex Anchor Substitutions Alter the Conformation of T Cell Receptor Contacts," *J. Biol. Chemistry* 276(24):21443-21449 (2001).

Sidransky et al., "Nucleic Acid-Based Methods for Detection of Cancer," *Science* 278:1054-1058 (1997).

Skolnick et al., "From genes to protein structure and function: novel applications of computational approaches in the genomic era," *TIBTECH* 18:34-39 (2000).

Spitler et al., "Cancer Vaccines: The Interferon Analogy," *Cancer Biotherapy* 10(1):1-3 (1995).

Tockman et al., "Considerations in Bringing a Cancer Biomarker to Clinical Application," *Cancer Research (Suppl.)* 52:2711-2718 (1992).

Turhan et al., "Cells in various benign and malignant conditions of the human prostate express different antigenic phenotypes," *Int. Urol. Nephrol.* 30(6):731-744 (1998) (Abstract Only).

Vasmatzis et al., "Discovery of three genes specifically expressed in human prostate by expressed sequence tag database analysis," *Proc. Natl. Acad. Sci. USA*, 95:300-304 (1998).

Walter et al., "A mutant human beta2-microglobulin can be used to generate diverse multimeric class I peptide complexes as specific probes for T cell receptors," *J. Immunol. Methods* 214:(1-2):41-50 (1998) (Abstract Only).

Ward, Anthony M., "Tumour Markers", *Kluwer Academic Publishers Group*, The Netherlands, 91-106.

Wolfgang et al., "TARP: A nuclear protein expressed in prostate and breast cancer cells derived from an alternate reading frame of the T cell receptor γ chain locus," *Proc. Natl. Acad. Sci USA*, 97(17):9437-9442 (2000).

Wolfgang et al., "T-cell receptor gamma chain alternate reading frame protein (TARP) expression in prostate cancer cells leads to an increased growth rate and induction of caveolins and amphiregulin," *Cancer Res.* 61(22):8122-8126, 2001.

Yoshikai, et al., "Repertoire of the human T cell gamma genes: high frequency of nonfunctional transcript in thymus and mature T cells," *Eur. J. Immunol.* 17(1):119-126 (1987) (Embl. Database Entry HSTCRGAA4, Accession No. M27334).

GenBank Accession No. M16768, Jan. 14, 1995.
GenBank Accession No. AAG29337, Nov. 30, 2000.
GenBank Accession No. AI557112, Mar. 23, 1999.
GenBank Accession No. CAA51166, Sep. 9, 1993.
GenBank Accession No. M27334, Jan. 14, 1995.
GenBank Accession No. X72500, Sep. 9, 1993.
GenBank Accession No. AF151103, Nov. 3, 2000.

\* cited by examiner

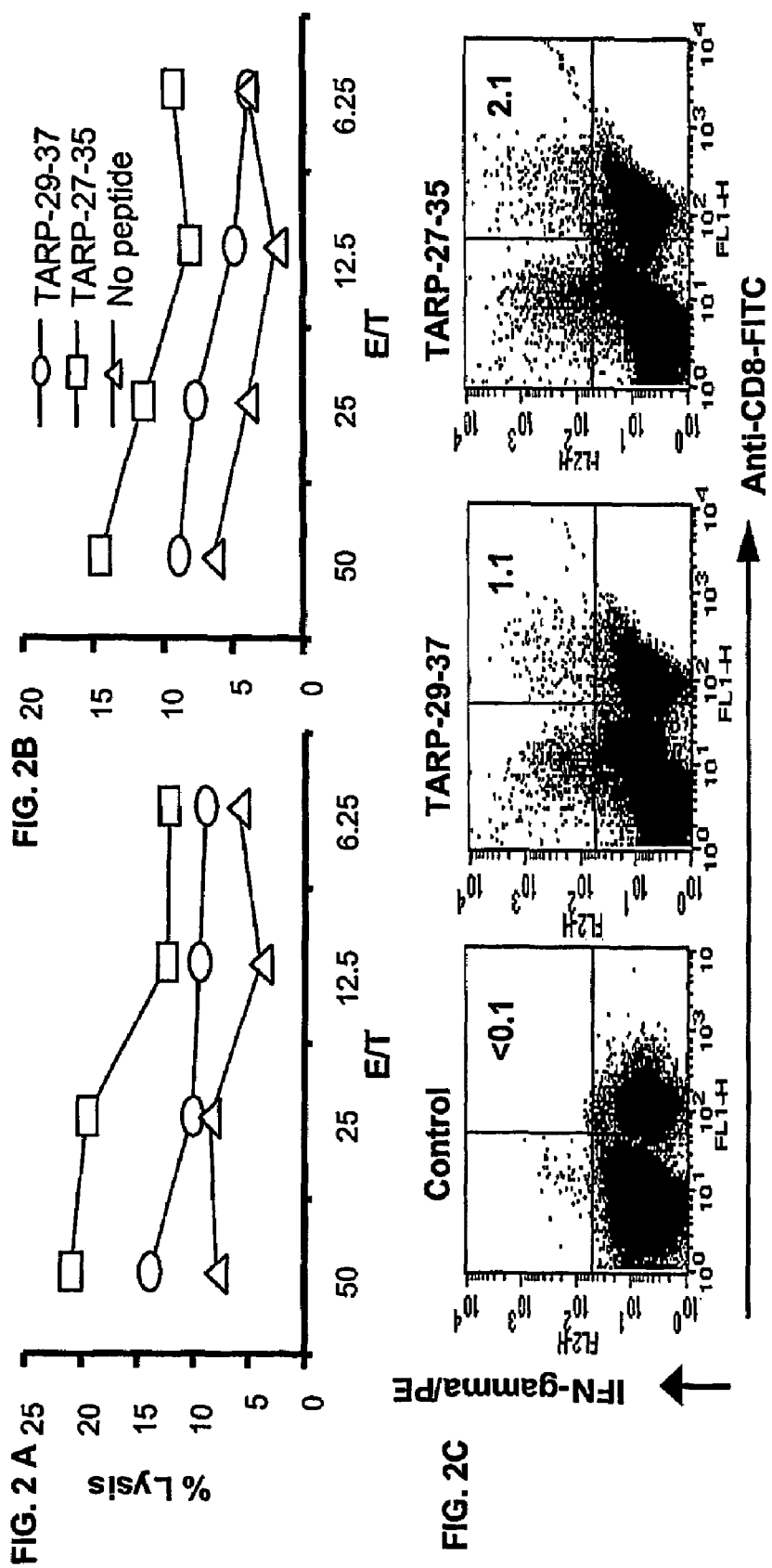

FIG. 3A Epitope-enhanced peptides
FLFLRNFSL (TARP-27-35-2L)    FLANFSLML (TARP-29-37-3A)
FVALRNFSL (TARP-27-35-3A)    FLRNFSLMV (TARP-29-37-9V)
FVFLRNFSV (TARP-27-35-9V)

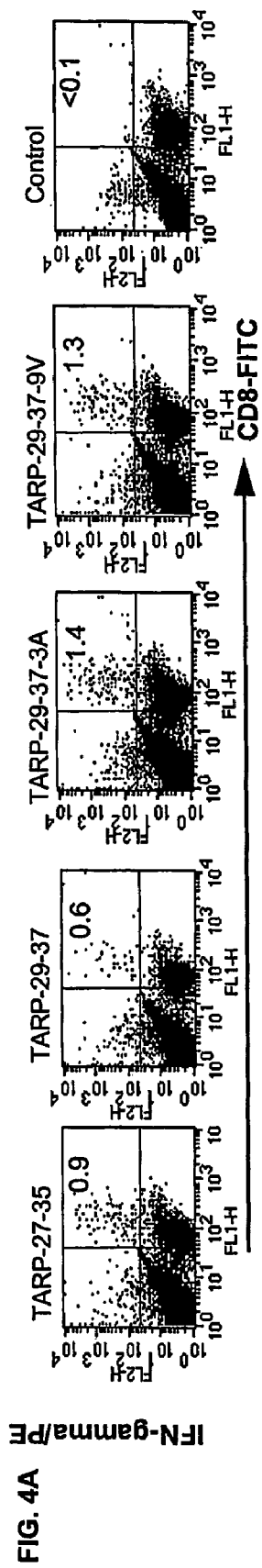
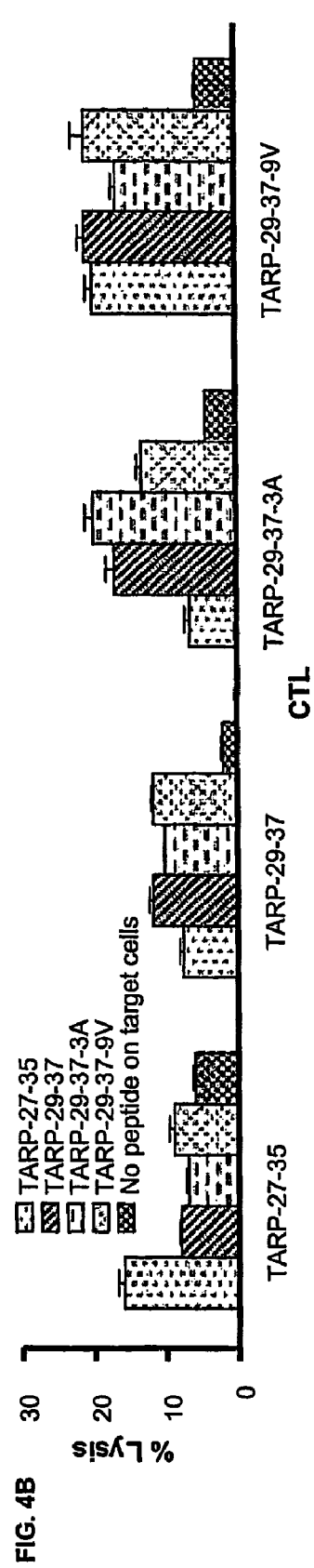
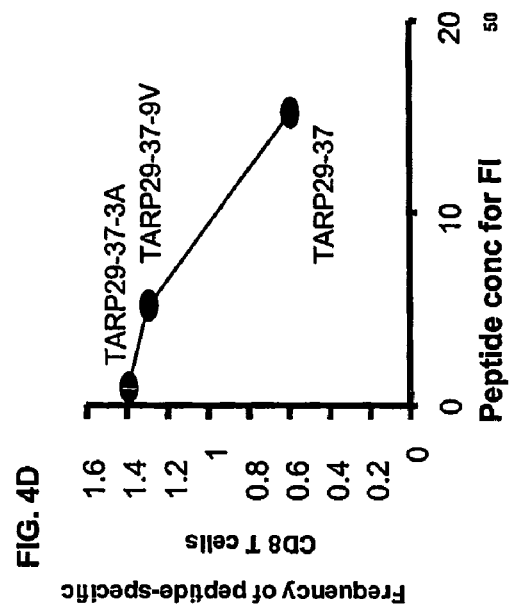
FIG. 4A
FIG. 4B
FIG. 4C
FIG. 4D

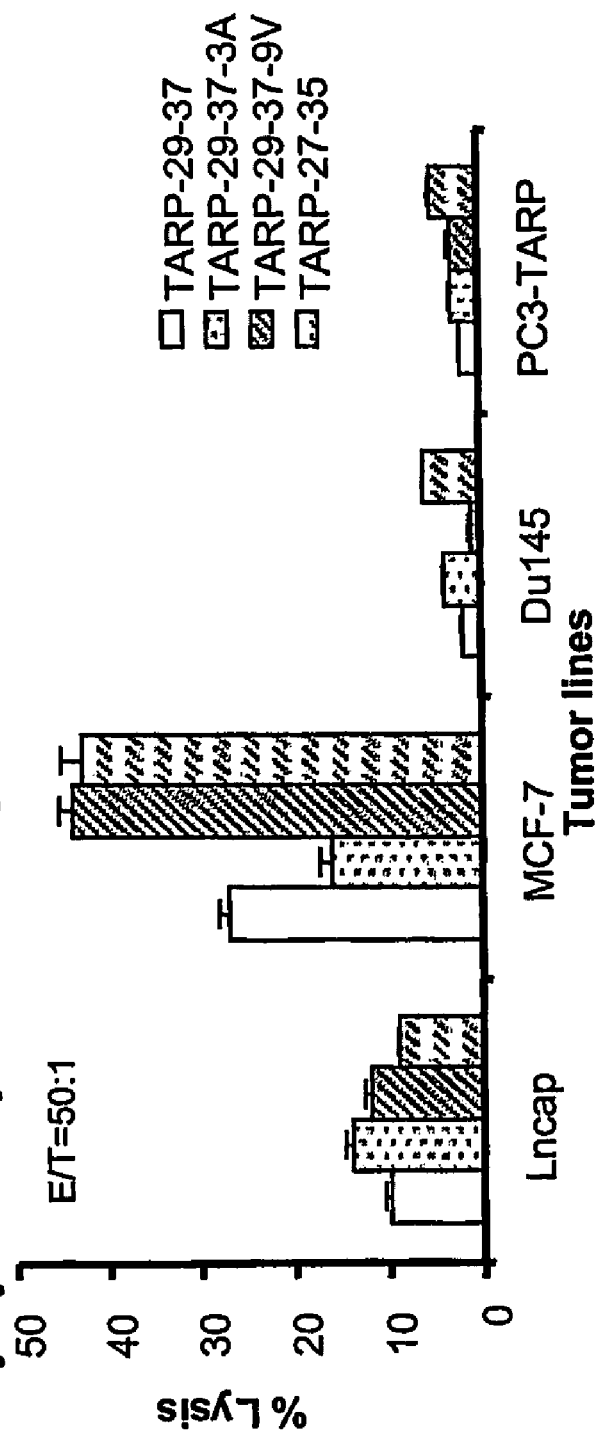
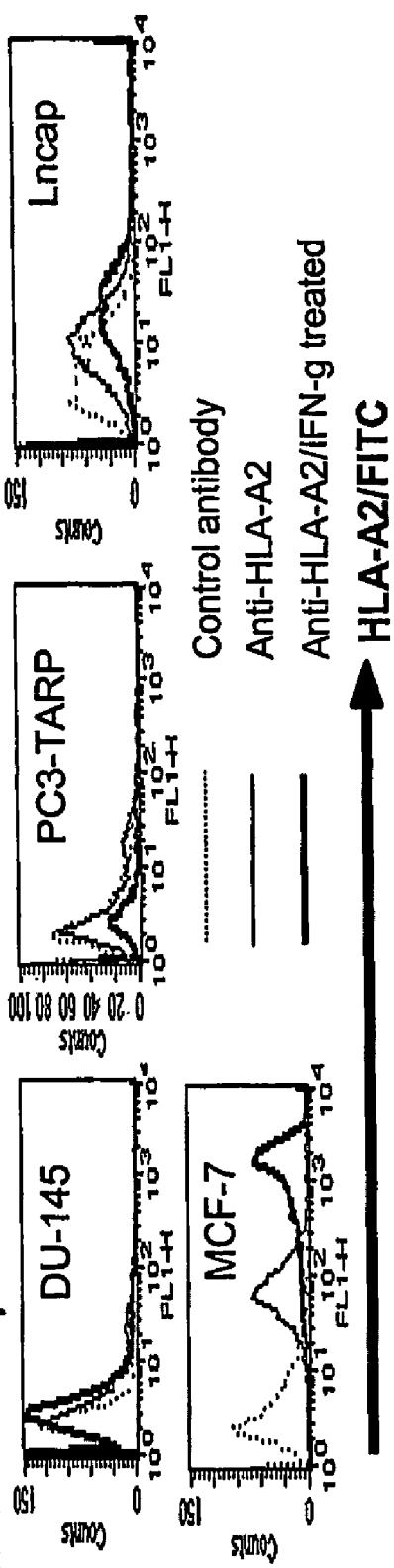
FIG. 7A Cytolytic activity of CD8 CTL against tumor lines
FIG. 7B HLA-A2 expressions on tumor lines

SEQUENCE LISTING

<160> NUMBER OF SEQ ID NOS: 9

<210> SEQ ID NO 1
<211> LENGTH: 58
<212> TYPE: PRT
<213> ORGANISM: Homo sapiens

<400> SEQUENCE: 1

Met Gln Met Phe Pro Pro Ser Pro Leu Phe Phe Leu Gln Leu Leu
1               5                   10                  15

Lys Gln Ser Ser Arg Arg Leu Glu His Thr Phe Val Phe Leu Arg Asn
                20                  25                  30

Phe Ser Leu Met Leu Leu Arg Tyr Ile Gly Lys Lys Arg Arg Ala Thr
            35                  40                  45

Arg Phe Trp Asp Pro Arg Arg Gly Thr Pro
    50                  55

<210> SEQ ID NO 2
<211> LENGTH: 1027
<212> TYPE: DNA
<213> ORGANISM: Homo sapiens

<400> SEQUENCE: 2
gggcaagagt tgggcaaaaa aatcaaggta tttggtcccg gaacaaagct tatcattaca      60
gataaacaac ttgatgcaga tgtttccccc aagcccacta tttttcttcc ttcaattgct     120
gaaacaaagc tccagaaggc tggaacatac ctttgtcttc ttgagaaatt tttccctgat     180
gttattaaga tacattggca agaaaagaag agcaacacga ttctgggatc ccaggagggg     240
aacaccatga agactaacga cacatacatg aaatttagct ggttaacggt gccagaaaag     300
tcactggaca agaacacag atgtatcgtc agacatgaga ataataaaaa cggagttgat      360
caagaaatta tctttcctcc aataaagacg gatgtcatca caatggatcc caaagacaat     420
tgttcaaaag atgcaaatga tacactactg ctgcagctca caaacacctc tgcatattac     480
atgtacctcc tcctgctcct caagagtgtg gtctattttg ccatcatcac ctgctgtctg     540
cttagaagaa cggctttctg ctgcaatgga gagaaatcat aacagacggt ggcacaagga     600
ggccatcttt tcctcatcgg ttattgtccc tagaagcgtc ttctgaggat ctagttgggc     660
tttctttctg ggtttgggcc atttcagttc tcatgtgtgt actattctat cattattgta     720
taacggtttt caaaccagtg ggcacacaga gaacctcact ctgtaataac aatgaggaat     780
agccacggcg atctccagca ccaatctctc catgttttcc acagctcctc cagccaaccc     840
aaatagcgcc tgctatagtg tagacatcct gcggcttcta gccttgtccc tctcttagtg     900
ttctttaatc agataactgc ctggaagcct ttcattttac acgccctgaa gcagtcttct     960
ttgctagttg aattatgtgg tgtgtttttc cgtaataagc aaaataaatt taaaaaaatg    1020
aaaagtt                                                              1027

<210> SEQ ID NO 3
<211> LENGTH: 9
<212> TYPE: PRT
<213> ORGANISM: Homo sapiens

<400> SEQUENCE: 3

Phe Leu Arg Asn Phe Ser Leu Met Leu
1               5

```
<210> SEQ ID NO 4
<211> LENGTH: 9
<212> TYPE: PRT
<213> ORGANISM: Homo sapiens

<400> SEQUENCE: 4

Phe Val Phe Leu Arg Asn Phe Ser Leu
1               5

<210> SEQ ID NO 5
<211> LENGTH: 9
<212> TYPE: PRT
<213> ORGANISM: Artificial Sequence
<220> FEATURE:
<223> OTHER INFORMATION: TARP peptide with a R3A substitution.

<400> SEQUENCE: 5

Phe Leu Ala Asn Phe Ser Leu Met Leu
1               5

<210> SEQ ID NO 6
<211> LENGTH: 9
<212> TYPE: PRT
<213> ORGANISM: Artificial Sequence
<220> FEATURE:
<223> OTHER INFORMATION: TARP peptide with a L9V substitution.

<400> SEQUENCE: 6

Phe Leu Arg Asn Phe Ser Leu Met Val
1               5

<210> SEQ ID NO 7
<211> LENGTH: 8
<212> TYPE: PRT
<213> ORGANISM: Homo sapiens

<400> SEQUENCE: 7

Gln Met Phe Pro Pro Ser Pro Leu
1               5

<210> SEQ ID NO 8
<211> LENGTH: 9
<212> TYPE: PRT
<213> ORGANISM: Homo sapiens

<400> SEQUENCE: 8

Arg Leu Glu His Thr Phe Val Phe Leu
1               5

<210> SEQ ID NO 9
<211> LENGTH: 11
<212> TYPE: PRT
<213> ORGANISM: Artificial Sequence
<220> FEATURE:
<223> OTHER INFORMATION: TARP consensus sequence.
<220> FEATURE:
<221> NAME/KEY: MISC_FEATURE
<222> LOCATION: (5)..(5)
<223> OTHER INFORMATION: "Xaa" equals Arg or Ala.
<220> FEATURE:
<221> NAME/KEY: MISC_FEATURE
<222> LOCATION: (11)..(11)
<223> OTHER INFORMATION: "Xaa" equals Leu or Val.

<400> SEQUENCE: 9

Phe Val Phe Leu Xaa Asn Phe Ser Leu Met Xaa
1               5                   10
```

US 7,541,035 B2

IMMUNOGENIC PEPTIDES FOR THE TREATMENT OF PROSTATE AND BREAST CANCER

CROSS REFERENCE TO RELATED APPLICATIONS

This is a § 371 U.S. national stage of PCT/US2004/017574, filed Jun. 2, 2004, which was published in English under PCT Article 2(2), and claims the benefit of U.S. Provisional Application No. 60/476,467, filed Jun. 5, 2003, which is incorporated by reference herein in its entirety.

FIELD

This application relates to the field of cancer therapeutics, specifically to immunogenic peptides and their use in the treatment of prostate and breast cancer.

BACKGROUND

Cancer of the prostate is the most commonly diagnosed cancer in men and is the second most common cause of cancer death (Carter and Coffey, *Prostate* 16:39-48, 1990; Armbruster et al., *Clinical Chemistry* 39:181, 1993). If detected at an early stage, prostate cancer is potentially curable. However, a majority of cases are diagnosed at later stages when metastasis of the primary tumor has already occurred (Wang et al., *Meth. Cancer Res.* 19:179, 1982). Even early diagnosis is problematic because not all individuals who test positive in these screens develop cancer.

Present treatment for prostate cancer includes radical prostatectomy, radiation therapy, or hormonal therapy. With surgical intervention, complete eradication of the tumor is not always achieved and the observed re-occurrence of the cancer (12-68%) is dependent upon the initial clinical tumor stage (Zietman et al., *Cancer* 71:959, 1993). Thus, alternative methods of treatment including prophylaxis or prevention are desirable.

Breast cancer is the most common type of epithelial cancer among women in the United States. More than 180,000 women are diagnosed with breast cancer each year. About one in eight women in the United States (approximately 12.8 percent) will develop breast cancer during her lifetime. At present there are no curative therapies available for breast cancer that has metastasized from its site of origination.

Up to 30% of 180,000 United States patients with potentially curable early-stage breast and prostate cancer will fail standard surgical or radiotherapy in 2004. In addition, patients with metastatic prostate cancer and the majority of patients with metastatic breast cancer enjoy limited benefit of standard chemotherapy and hormone-based therapies. Immunotherapy may have great potential to improve on these results, combining the tumor specificity of cell-mediated immunity with freedom from toxic chemotherapies.

Immunotherapy involves evoking an immune response against cancer cells based on their production of target antigens. Immunotherapy based on cell-mediated immune responses involves generating a cell-mediated response to cells that produce particular antigenic determinants, while immunotherapy based on humoral immune responses involves generating specific antibodies to cells that produce particular antigenic determinants.

Recent studies show that immunotherapy of cancer patients may be dramatically improved by the finding that $CD8^+$ CTL recognize and kill tumor cells that display peptides from tumor-associated antigens within MHC Class I molecules. In clinical studies it has been found that effector $CD8^+$ T cells play a major role in tumor regression. Several tumor antigens in prostate cancer models have been identified and HLA allele-specific peptides from those prostate cancer-associated antigens have been identified as $CD8^+$ T cell epitopes. For example, HLA-A2.1 binding peptides were described that were derived from prostate specific antigen (PSA) (Correale et al., *J Immunol* 161:3186, 1998), prostate-specific membrane antigen (PSMA) (Tjoa et al., *Prostate* 28:65, 1996), prostate stem cell antigen (PSCA) (Kiessling et al., *Int J Cancer* 102:390, 2002), and prostate acid phosphatase (Peshwa et al., *Prostate* 36:129, 1998). For PSA, clinical trials are in progress using different vaccine strategies. However, there clearly is a need to identify additional antigens to aid in the diagnosis of prostate cancer, and for use as additional therapeutic agents.

SUMMARY

Immunogenic T cell receptor gamma Alternate Reading Frame Protein (TARP) polypeptides are disclosed herein. These immunogenic TARP polypeptides include nine consecutive amino acids of the amino acid sequence set forth as SEQ ID NO: 9 and do not comprise consecutive amino acids 1-26 or consecutive amino acids 38-58 of SEQ ID NO: 1. Several specific, non-limiting examples of these polypeptides are set forth as SEQ ID NOs: 3-7. Nucleic acids encoding these polypeptides, and host cells transfected with these nucleic acids, are also disclosed.

The polypeptides are of use in generating an immune response to TARP, such as, but not limited to, a T cell response. Specifically, these polypeptides can be used to generate an immune response to breast cancer and prostate cancer cells that express TARP.

In one embodiment, the immunogenic TARP polypeptides, or a nucleic acid encoding the polypeptide, are administered to a subject to produce an immune response to TARP. In another embodiment, specific antigen presenting cells are prepared by contacting dendritic cells with an immunogenic TARP polypeptide. These antigen presenting cells are administered to a subject. In a further embodiment, the antigen presenting cells are used to generate cytotoxic T cells that specifically recognize TARP. The cytotoxic T cells are administered to a subject. For each of these embodiments, the subject can have breast cancer or prostate cancer, and the cells of the cancer express TARP.

Also disclosed herein is a reagent that includes a tetramer of the immunogenic TARP polypeptide bound to HLA-A.2.1, wherein the reagent is labeled or unlabeled. This reagent is of use in identifying CD8+ cells that specifically bind TARP.

The foregoing and other features and advantages will become more apparent from the following detailed description of several embodiments, which proceeds with reference to the accompanying figures.

BRIEF DESCRIPTION OF THE FIGURES

FIG. 1A is the amino acid sequence of the TARP protein (SEQ ID NO: 1). FIG. 1B is the sequence of the predicted-HLA-A2.1-binding peptides (amino acids 2-9, 22-30, 29-37 and 27-25 of SEQ ID NO: 1). FIG. 1C is a line graph of a T2 binding assay. Peptides were dissolved in double-distilled water (DDW) or 20% DMSO in DDW, and then different concentrations of peptides were added into the culture of TAP-deficient T2 cells. After overnight culture of the cells in medium supplemented with β-2 microglobulin, cells were stained with anti-HLA-A2. Each assay was performed in triplicate assay and data in this figure are representative of two experiments with similar results.

FIGS. 2A-C are line graphs and data plots from fluorescence activated cell sorting experiments. Immunization with peptide-loaded dendritic cell (DC) or a DNA plasmid expressing TARP results in peptide-specific CD8$^+$ T cell responses in A2K$^b$ transgenic mice. To obtain the data for the graph shown in FIG. 2A, mice were immunized subcutaneously with peptide-loaded (10 µM of TARP-29-37 or TARP-27-35) bone marrow-derived DC and boosted twice at three-week intervals. To obtain the data for the graph shown in FIG. 2B, mice were immunized with 100 µg of DNA plasmid intramuscularly and boosted four times at three-week intervals. For the data shown in FIGS. 2A and 2B, after the final immunization, spleen CD8$^+$ T cells were restimulated with splenocytes in media containing 10 µM soluble peptides for 7 days. In a 5 hour $^{51}$Cr-release assay, Jurkat cells transfected with HLA-A2 were labeled with $^{51}$Cr, and then pulsed with 10 µM of peptides. Without washing, target cells were mixed with different numbers of effector cells for 5 hours before harvesting. For the data plots shown in FIG. 2C, for intracellular cytokine staining, CD8$^+$ T cells from the mice immunized with peptide-pulsed DC were stimulated with the identical peptide and treated with Brefeldin A for 5 hour, and then cells were stained with anti-CD8-FITC and IFN-γ-PE as described in the manufacturer's protocol (Pharmingen). In each experiment, pooled-spleen CD8$^+$ T cells of 3 mice were tested. Data are representative of two repeated experiments with similar results (SE<10%).

FIGS. 3A-C are peptide sequences and two line graphs showing HLA-A2.1 epitope-enhancement by amino acid substitutions in the wild-type peptides. FIG. 3A is the amino acid sequences of predicted enhanced epitopes (SEQ ID NO: 4, wherein L is at position 2, A is at position 3 or wherein V is at position 9, SEQ ID NO: 5 and SEQ ID NO: 6). FIGS. 3B and 3C are graphs showing the binding affinity of the substituted TARP27-35 peptides (FIG. 3B) or the substituted TARP27-37 peptides (FIG. 3C) to HLA-A2 molecules. Peptides were dissolved in double-distilled water or 20% DMSO, and then different concentrations of peptides were added into the culture of TAP-deficient T2 cells. After overnight culture of the cells in medium supplemented with β2-microglobulin, cells were stained with anti-HLA-A2. Each assay was performed in triplicate, and data in this figure are representative of two experiments with similar results.

FIGS. 4A-D are FACS plots, a bar graph and two line graphs showing the immunogenicity of the enhanced epitopes in A2K$^b$ transgenic mice. A2K$^b$ transgenic mice were immunized subcutaneously with the mixture of peptide and cytokine in adjuvant as described in the Examples section. For the data plotted in FIG. 4A, two weeks after second boost, pooled-spleen CD8$^+$ T cells from 3-4 mice were restimulated with 1.0 µM of each peptide. During restimulation, CD8$^+$ T cells were treated with Brefeldin A for 5 hours. Cells were stained with anti-CD8-FITC and IFN-γ-PE as described in the manufacturer's protocol (Pharmingen). FIG. 4B is a bar graph showing the cross-reactivity on each peptide (E:T=100:1). Two weeks after the second boost, pooled spleen CD8$^+$ T cells from three to four mice were restimulated with irradiated splenocytes in medium containing 1.0 µM each peptide for 7 days. In a 5-hour $^{51}$Cr release assay, Jurkat cells transfected with HLA-A2 were labeled with $^{51}$Cr and then pulsed with peptides. Without washing, target cells were mixed with different numbers of effector cells and then cultured for 5 hours before harvesting. FIG. 4C is a line graph showing data obtained when CTLs raised against the individual peptides indicated were tested on target cells pulsed with either wild-type TARP29-37 (closed symbols) or no peptide (open symbols). Lytic activity is shown as a function of E:T ratio. Bars represent SE in triplicate assay, and bars smaller than the symbols are not shown. FIG. 4D is a line graph showing the relationship between peptide binding affinity and immunogenicity of each peptide. Peptide concentrations for fluorescence index value=0.5 (FI$_{50}$) from FIG. 3 were plotted versus the numbers of IFN-γ-producing cells (see FIG. 4A). Data were reproducible in two repeated experiments with similar results.

FIGS. 7A-B are a bar graph and plots showing human CD8$^+$ CTL raised by in vitro restimulation kill human cancer cell line. For FIG. 7A, in a 5-hour $^{51}$Cr release assay, LNCaP (prostate cancer cell line; HLA-A2$^+$TARP$^+$), MCF-7 (breast cancer cell line; HLA-A2$^+$TARP$^+$), DU145 (prostate cancer cell line; HLA-A2$^-$TARP$^-$), and PC3-TARP (prostate cancer cell line transfected with TARP; HLA-A2$^-$TARP$^+$) were used as target cells. Target cells were pre-incubated with 1000 ng/ml human IFN-γ for 72 hours. Data are representative of two repeated experiments with similar results, and error bars (SEM) were calculated from a triplicate assay in one experiment. For the results shown in FIG. 7B, tumor cell lines were stained with anti-HLA-A2 after incubation with or without IFN-γ for 72 hours.

SEQUENCE LISTING

Figure 1:
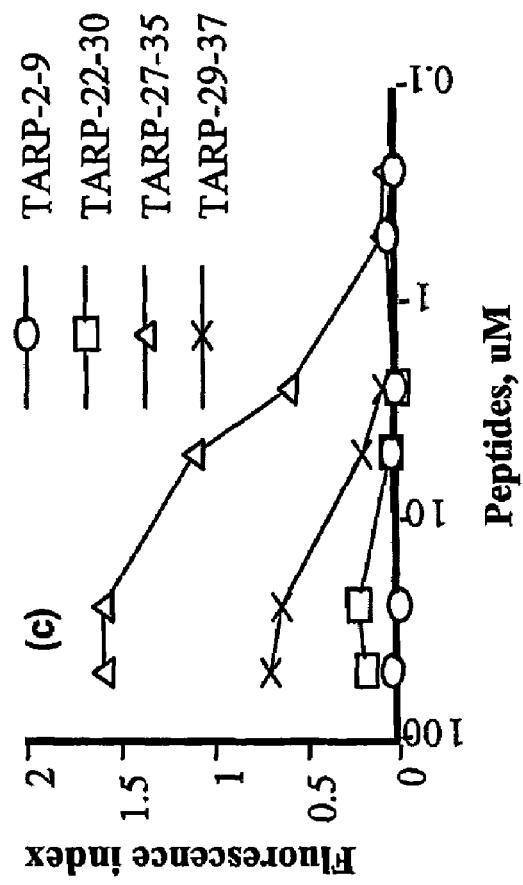
FIGS. 1A-C are polypeptide sequences of TARP (SEQ ID NO: 1), wild-type HLA-A2 epitopes (amino acids 2-9, 22-30, 29-37 and 27-25 of SEQ ID NO: 1), and a line graph showing their binding affinities to HLA-A2.1 molecules.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is an amino acid sequence of a full-length TCRγ Alternate Reading Frame Protein (TARP) protein.

SEQ ID NO: 2 is a nucleic acid sequence encoding a full-length TARP protein.

SEQ ID NO: 3 is the amino acid sequence of TARP-29-37, which corresponds to amino acids 29-37 of SEQ ID NO: 1.

SEQ ID NO: 4 is the amino acid sequence of TARP-27-35, which corresponds to amino acids 27-35 of SEQ ID NO: 1.

SEQ ID NO: 5 is the amino acid sequence of TARP-29-37-3A, which corresponds to amino acids 29-37 of SEQ ID NO: 1, with a single substitution.

SEQ ID NO: 6 is the amino acid sequence of TARP-29-37-9V, which corresponds to amino acids 29-37 of SEQ ID NO: 1, with a single substitution.

SEQ ID NO: 7 is the amino acid sequence of TARP-2-9, which corresponds to amino acids 2-9 of SEQ ID NO: 1.

SEQ ID NO: 8 is the amino acid sequence of TARP-22-30, which corresponds to amino acids 22-30 of SEQ ID NO: 1.

SEQ ID NO: 9 is the consensus sequence for an immunogenic TARP polypeptide. This sequence corresponds to amino acids 27-37 of SEQ ID NO: 1, with zero, one or two substitutions.

DETAILED DESCRIPTION

I. Abbreviations

APC: antigen presenting cell
CTL: cytotoxic T lymphocyte
DC: dendritic cell
DDW: double distilled water
DMSO: dimethyl sulfoxide
E/T: effector to target
FACS: fluorescence activated cell sorting
FITC: fluorescein isothiocyanate
Flt-3L: flt-3 ligand
GM-CSF: granulocyte/macrophage colony stimulating factor
HLA: human major histocompatibility complex
IL-4: interleukin-4
MHC: Major Histocompatibility Complex
PBL: peripheral blook lymphocytes
PBMC: peripheral blood mononuclear cells
PE: phycoerythrin
TARP: TCRγ Alternate Reading Frame Protein
TCR: T cell receptor
TIL: tumor infiltrating lymphocytes
μM: micromolar

II. Terms

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Adjuvant: A vehicle used to enhance antigenicity; such as a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunstimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199).

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and 2-dimensional nuclear magnetic resonance.

An antigen can be a tissue-specific antigen, or a disease-specific antigen. These terms are not exclusive, as a tissue-specific antigen can also be a disease specific antigen. A tissue-specific antigen is expressed in a limited number of tissues, such as a single tissue. Specific, non-limiting examples of a tissue specific antigen are a prostate specific antigen and/or a breast specific antigen. A tissue specific antigen may be expressed by more than one tissue, such as, but not limited to, an antigen that is expressed in both prostate and breast tissue. A disease-specific antigen is expressed coincidentally with a disease process. Specific non-limiting examples of a disease-specific antigen are an antigen whose expression correlates with, or is predictive of, tumor formation, such as prostate cancer and/or breast cancer. A disease-specific antigen can be an antigen recognized by T cells or B cells.

Amplification: Of a nucleic acid molecule (e.g., a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification can be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, i.e., molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the VL and VH domains of a single arm of an antibody, (iv) a dAb fragment (Ward et al., Nature 341:544-546, 1989) which consists of a $V_H$ domain; (v) an isolated complimentarity determining region (CDR); and (vi) a F(ab')$_2$ fragment, a bivalent fragment comprising two Fab fragments linked by a disulfide bridge at the hinge region.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., Nature 298:286, 1982; Morrison, J. Immunol. 123:793, 1979; Morrison et al., Ann Rev. Immunol 2:239, 1984).

Animal: Living multi-cellular vertebrate organisms, a category that includes, for example, mammals and birds. The term mammal includes both human and non-human mammals. Similarly, the term "subject" includes both human and veterinary subjects.

Breast cancer: A neoplastic condition of breast tissue that can be benign or malignant. The most common type of breast cancer is ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV).

Conservative variants: "Conservative" amino acid substitutions are those substitutions that do not substantially affect or decrease an activity or antigenicity of an antigenic epitope of TARP. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |

-continued

| Original Residue | Conservative Substitutions |
| --- | --- |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Cancer: A malignant neoplasm that has undergone characteristic anaplasia with loss of differentiation, increase rate of growth, invasion of surrounding tissue, and is capable of metastasis. For example, prostate cancer is a malignant neoplasm that arises in or from prostate tissue, and breast cancer is a malignant neoplasm that arises in or from breast tissue (such as a ductal carcinoma). Residual cancer is cancer that remains in a subject after any form of treatment given to the subject to reduce or eradicate thyroid cancer. Metastatic cancer is a cancer at one or more sites in the body other than the site of origin of the original (primary) cancer from which the metastatic cancer is derived.

CD4: Cluster of differentiation factor 4, a T cell surface protein that mediates interaction with the MHC Class II molecule. CD4 also serves as the primary receptor site for HIV on T cells during HIV infection. Cells that express CD4 are often helper T cells.

CD8: Cluster of differentiation factor 8, a T cell surface protein that mediates interaction with the MHC Class I molecule. Cells that express CD8 are often cytotoxic T cells.

Chemotherapy; chemotherapeutic agents: As used herein, any chemical agent with therapeutic usefulness in the treatment of diseases characterized by abnormal cell growth. Such diseases include tumors, neoplasms and cancer as well as diseases characterized by hyperplastic growth such as psoriasis. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology $2^{nd}$ ed., © 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). The immunogenic TARP polypeptides disclosed herein can be used in conjunction with additional chemotherapeutic agents.

Degenerate variant: A polynucleotide encoding an epitope of TARP that includes a sequence that is degenerate as a result of the genetic code. There are 20 natural amino acids, most of which are specified by more than one codon. Therefore, all degenerate nucleotide sequences are included in this disclosure as long as the amino acid sequence of the TARP polypeptide encoded by the nucleotide sequence is unchanged.

Dendritic cell (DC): Dendritic cells are the principle antigen presenting cells (APCs) involved in primary immune responses. Dendritic cells include plasmacytoid dendritic cells and myeloid dendritic cells. Their major function is to obtain antigen in tissues, migrate to lymphoid organs and present the antigen in order to activate T cells. Immature dendritic cells originate in the bone marrow and reside in the periphery as immature cells.

Diagnostic: Identifying the presence or nature of a pathologic condition, such as, but not limited to, prostate cancer. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as prostate cancer, or metastasis.

Epitope: An antigenic determinant. These are particular chemical groups or peptide sequences on a molecule that are antigenic, i.e. that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8 to 10 amino acids in a unique spatial conformation. Methods of determining spatial conformation of epitopes include, for example, x-ray crystallography and 2-dimensional nuclear magnetic resonance. See, e.g., "Epitope Mapping Protocols" in *Methods in Molecular Biology*, Vol. 66, Glenn E. Morris, Ed (1996). In one embodiment, an epitope binds an MHC molecule, such an HLA molecule or a DR molecule. These molecules bind polypeptides having the correct anchor amino acids separated by about eight to about ten amino acids, such as nine amino acids.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like can be used. In one embodiment, when cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Heterologous: Originating from separate genetic sources or species. A polypeptide that is heterologous to TARP originates from a nucleic acid that does not encode TARP. In one specific, non-limiting example, a polypeptide comprising nine consecutive amino acids from TARP and a heterologous amino acid sequence includes a β-galactosidase, a maltose binding protein, and albumin, or an immunoglobulin amino acid sequence. Generally, an antibody that specifically binds to a protein of interest will not specifically bind to a heterologous protein.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a CD8+ response. In another embodiment, the response is a B cell response, and results in the production of specific antibodies.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein (e.g. HLA-A02.01) and by their ability to stimulate CD4 and/or CD8 when presented in the context of the MHC protein.

Immunogenic composition: A composition comprising an epitope of a TARP polypeptide that induces a measurable CTL response against cells expressing TARP polypeptide, or induces a measurable B cell response (e.g., production of antibodies that specifically bind TARP) against a TARP polypeptide. It further refers to isolated nucleic acids encoding an immunogenic epitope of TARP polypeptide that can be used to express the epitope (and thus be used to elicit an immune response against this polypeptide). For in vitro use, the immunogenic composition can consist of the isolated nucleic acid protein or peptide. For in vivo use, the immunogenic composition will typically comprise the nucleic acid protein or peptide in pharmaceutically acceptable carriers, and/or other agents. A TARP polypeptide, or nucleic acid encoding the polypeptide, can be readily tested for its ability to induce a CTL by art-recognized assays.

Inhibiting or treating a disease: Inhibiting a disease, such as tumor growth, refers to inhibiting the full development of a disease. In several examples, inhibiting a disease refers to lessening symptoms of a tumor, such as preventing the development of paraneoplastic syndrome in a person who is known to have prostate or breast cancer, or lessening a sign or symptom of the tumor. "Treatment" refers to a therapeutic intervention that ameliorates a sign or symptom of a disease or pathological condition related to the disease, such as the tumor.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker sequence: A linker sequence is an amino acid sequence that covalently links two polypeptide domains. Linker sequences can be included in the between the TARP epitopes disclosed herein to provide rotational freedom to the linked polypeptide domains and thereby to promote proper domain folding and presentation to the MHC. By way of example, in a recombinant polypeptide comprising two TARP-29-37-9V (SEQ ID NO: 6) domains, linker sequences can be provided between them, such as a polypeptide comprising TARP-29-37-9V (SEQ ID NO: 6)-linker-TARP-29-37-9V (SEQ ID NO: 6). Linker sequences, which are generally between 2 and 25 amino acids in length, are well known in the art and include, but are not limited to, the glycine(4)-serine spacer (GGGGS x3) described by Chaudhary et al., *Nature* 339:394-397, 1989.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Neoplasm: An abnormal cellular proliferation, which includes benign and malignant tumors, as well as other proliferative disorders.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Peptide: A chain of amino acids of between 3 and 30 amino acids in length. In one embodiment, a peptide is from about 7 to about 25 amino acids in length. In yet another embodiment, a peptide is from about 8 to about 10 amino acids in length. In yet another embodiment, a peptide is about 9 amino acids in length.

Peptide Modifications: TARP epitopes include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this invention to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an immunogenic TARP polypeptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a chemical composition or a cell to achieve a desired effect in a subject being treated. For instance, this can be the amount necessary to inhibit tumor growth or to measurably alter outward symptoms of the tumor. When administered to a subject, a dosage will generally be used that will achieve target tissue concentrations (for example, in lymphocytes) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). In one embodiment, the polypeptide is a TARP polypeptide.

Probes and primers: A probe comprises an isolated nucleic acid attached to a detectable label or reporter molecule. Primers are short nucleic acids, preferably DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers can be selected that comprise about 20, 25, 30, 35, 40, 50 or more consecutive nucleotides.

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Specific, non-limiting examples of promoters include promoters derived from the genome of mammalian cells (e.g., metallothionein promoter) or from mammalian viruses (e.g., the retrovirus long terminal repeat; the adenovirus late promoter; the vaccinia virus 7.5K promoter) can be used. Promoters produced by recombinant DNA or synthetic techniques can also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Prostate Cancer: A malignant tumor, generally of glandular origin, of the prostate. Prostate cancers include adenocarcinomas and small cell carcinomas. Many prostate cancers express prostate specific antigen (PSA).

Protein Purification: The epitopes of TARP disclosed herein can be purified (and/or synthesized) by any of the means known in the art (see, e.g., *Guide to Protein Purification*, ed. Deutscher, *Meth. Enzymol.* 185, Academic Press, San Diego, 1990; and Scopes, *Protein Purification: Principles and Practice*, Springer Verlag, New York, 1982). Substantial purification denotes purification from other proteins or cellular components. A substantially purified protein is at least about 60%, 70%, 80%, 90%, 95%, 98% or 99% pure. Thus, in one specific, non-limiting example, a substantially purified protein is 90% free of other proteins or cellular components.

Purified: The term purified does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. In one embodiment, a preparation is purified such that the protein or peptide represents at least about 60% (such as, but not limited to, 70%, 80%, 90%, 95%, 98% or 99%) of the total peptide or protein content of the preparation.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2× SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a TARP polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a TARP polypeptide are typically characterized by possession of at least 75%, for example at least 80%, sequence identity counted over the full length alignment with the amino acid sequence of TARP using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a TARP specific binding agent is an agent that binds substantially to a TARP polypeptide. In one embodiment, the specific binding agent is a monoclonal or polyclonal antibody that specifically binds TARP.

Subject: Living multi-cellular vertebrate organisms, a category that includes both human and veterinary subjects, including human and non-human mammals.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, a CD8 T cell is a cytotoxic T lymphocyte. In another embodiment, a CD8 cell is a suppressor T cell.

T cell receptor γ Alternate Reading frame Protein (TARP): A polypeptide that is translated from a form of the T cell receptor γ gene, which is transcribed in prostate cells of epithelial origin, in prostate cancer cells, and in many breast cancers. TARP is disclosed in published PCT Application No. WO 01/04309, published Jan. 18, 2001 (Pastan et al.), which is incorporated herein by reference.

In one embodiment, the polypeptide has a sequence set forth as:

MQMFPPSPLF FFLQLLKQSS RRLEHTF VFL RNFSLMLLRY IGKKRRATRF WDPRRGTP (SEQ ID NO: 1, see also GENBANK® Accession No. AAG29337, which is herein incorporated by reference).

In other embodiments, TARP has an amino acid sequence least 90% identical to SEQ ID NO: 1, for example a polypeptide that has about 91%, 92%, 93%, 94%, 95%, 96%, 97%, 98% or even higher sequence identity to SEQ ID NO: 1. Additional variants have been described (see below and see published PCT Application No. WO 01/04309 herein incorporated by reference, for a complete description of these polypeptides).

In another embodiment, TARP is encoded by nucleic acid having a sequence set forth as:

```
gggcaagagt tgggcaaaaa aatcaaggta tttggtcccg gaacaaagct tatcattaca gataaacaac ttgatgcaga tgtttccccc aagcccacta tttttcttcc ttcaattgct gaaacaaagc tccagaaggc tggaacatac ctttgtcttc ttgagaaatt tttccctgat gttattaaga tacattggca agaaaagaag agcaacacga ttctgggatc ccaggagggg aacaccatga agactaacga cacatacatg aaatttagct ggttaacggt gccagaaaag tcactggaca aagaacacag atgtatcgtc agacatgaga ataataaaaa cggagttgat caagaaatta tctttcctcc aataaagacg gatgtcatca caatggatcc caaagacaat tgttcaaaag atgcaaatga tacactactg ctgcagctca caaacacctc tgcatattac atgtacctcc tcctgctcct caagagtgtg gtctattttg ccatcatcac ctgctgtctg cttagaagaa cggctttctg ctgcaatgga gagaaatcat aacagacggt ggcacaagga ggccatcttt tcctcatcgg ttattgtccc tagaagcgtc ttctgaggat ctagttgggc tttctttctg ggtttgggcc atttcagttc tcatgtgtgt actattctat cattattgta taacggtttt caaaccagtg ggcacacaga gaacctcact ctgtaataac aatgaggaat agccacggcg atctccagca ccaatctctc catgttttcc acagctcctc cagccaaccc aaatagcgcc tgctatagtg tagacatcct gcggcttcta gccttgtccc tctcttagtg ttctttaatc agataactgc ctggaagcct ttcattttac acgccctgaa gcagtcttct ttgctagttg aattatgtgg tgtgttttc cgtaataagc aaaataaatt taaaaaaatg aaaagtt
```

(SEQ ID NO: 2, see also GENBANK® Accession No. AF151103, which is herein incorporated by reference).

See also Wolfgang et al., *Proc. Natl. Acad. Sci. U.S.A.* 97 (17):9437-9442, 2000, and WO 01/04309, published Jan. 18, 2001 (Pastan et al.), which is incorporated herein by reference.

Therapeutically active polypeptide: An agent, such as an epitope of TARP that causes induction of an immune response, as measured by clinical response (for example increase in a population of immune cells, increased cytolytic activity against cells that express TARP, or measurable reduction of tumor burden). Therapeutically active molecules can also be made from nucleic acids. Examples of a nucleic acid based therapeutically active molecule is a nucleic acid sequence that encodes a TARP epitope, wherein the nucleic acid sequence is operably linked to a control element such as a promoter.

In one embodiment, a therapeutically effective amount of an epitope of TARP is an amount used to generate an immune response, or to treat prostate cancer or breast cancer in a subject. Specific, non-limiting examples are a polypeptide having a sequence set forth as SEQ ID NOs: 3-7. Treatment refers to a therapeutic intervention that ameliorates a sign or symptom of prostate cancer or breast cancer, or a reduction in tumor burden.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Immunogenic TARP Peptides

T cell receptor γ Alternate Reading frame Protein (TARP) is a polypeptide that is translated from a form of the T cell receptor γ gene, which is transcribed in prostate cells of epithelial origin, in prostate cancer cells, and in many breast cancers. TARP is disclosed in published PCT Application No. WO 01/04309, published Jan. 18, 2001 (Pastan et al.), which is incorporated herein by reference.

In one embodiment, the polypeptide has a sequence set forth as:

MQMFPPSPLF FFLQLLKQSS RRLEHTF VFL RNFSLMLLRY IGKKRRATRF WDPRRGTP (SEQ ID NO: 1, see also GenBank Accession No. AAG29337, which is herein incorporated by reference).

In other embodiments, TARP has an amino acid sequence least 90% identical to SEQ ID NO: 1, for example a polypeptide that has about 91%, 92%, 93%, 94%, 95%, 96%, 97%, 98% or even higher sequence identity to SEQ ID NO: 1. Additional variants have been described (see below and see published PCT Application No. WO 01/04309 herein incorporated by reference, for a complete description of these polypeptides).

In another embodiment, TARP is encoded by a nucleic acid having a sequence set forth as:

```
gggcaagagt tgggcaaaaa aatcaaggta tttggtcccg gaacaaagct tatcattaca gataaacaac ttgatgcaga tgtttccccc aagcccacta tttttcttcc ttcaattgct gaaacaaagc tccagaaggc tggaacatac ctttgtcttc ttgagaaatt tttccctgat gttattaaga tacattggca agaaaagaag agcaacacga ttctgggatc ccaggagggg aacaccatga agactaacga cacatacatg aaatttagct ggttaacggt gccagaaaag tcactggaca aagaacacag atgtatcgtc agacatgaga ataataaaaa cggagttgat caagaaatta tctttcctcc aataaagacg gatgtcatca caatggatcc caaagacaat tgttcaaaag atgcaaatga tacactactg ctgcagctca caaacacctc tgcatattac atgtacctcc tcctgctcct caagagtgtg gtctattttg ccatcatcac ctgctgtctg cttagaagaa cggctttctg ctgcaatgga gagaaatcat aacagacggt ggcacaagga ggccatcttt tcctcatcgg ttattgtccc tagaagcgtc ttctgaggat ctagttgggc tttctttctg ggtttgggcc atttcagttc tcatgtgtgt actattctat cattattgta taacggtttt caaaccagtg ggcacacaga gaacctcact ctgtaataac aatgaggaat agccacggcg atctccagca ccaatctctc catgttttcc acagctcctc cagccaaccc aaatagcgcc tgctatagtg tagacatcct gcggcttcta gccttgtccc tctcttagtg ttctttaatc agataactgc ctggaagcct ttcattttac acgccctgaa gcagtcttct ttgctagttg aattatgtgg tgtgtttttc cgtaataagc aaaataaatt taaaaaaatg aaaagtt
```

(SEQ ID NO: 2, see also GenBank Accession No. AF151103, which is herein incorporated by reference). See also Wolfgang et al., *Proc. Natl. Acad. Sci. U.S.A.* 97(17):9437-9442, 2000, and WO 01/04309, published Jan. 18, 2001 (Pastan et al.), which is incorporated herein by reference. Immunogenic fragments of TARP and TARP itself, can also be chemically synthesized by standard methods. If desired, polypeptides can also be chemically synthesized by emerging technologies. One such process is described in W. Lu et al., *Federation of European Biochemical Societies Letters.* 429:31-35, 1998. Polypeptides can also be produced using molecular genetic techniques, such as by inserting a nucleic acid encoding TARP or an epitope thereof into an expression vector, introducing the expression vector into a host cell, and isolating the polypeptide (see below).

Immunogenic TARP polypeptides are disclosed herein. These peptides include nine consecutive amino acids from the consensus sequence:

FVF LX$_1$NFSLMX$_2$ (SEQ ID NO: 9), wherein X$_1$ is R or A, and wherein X$_2$ is L or V.

SEQ ID NO: 9 is equivalent to amino acids 27 to 37 of SEQ ID NO: 1, wherein amino acid 31 is an R or an A and wherein amino acid 37 is an L or a V. It should be note that in SEQ ID NO: 1, amino acid 31 is an R and amino acid 37 is a L. In one specific, non-limiting example, X$_1$ is an A and X$_2$ is an L. In other specific non-limiting examples, X$_1$ is A and X$_2$ is V, X$_1$ is R and X$_2$ is L, or X$_1$ is R and X$_2$ is V.

The immunogenic TARP polypeptides disclosed herein does not include all the additional consecutive amino acids of TARP (SEQ ID NO: 1). In one embodiment, the polypeptide does not include amino acids 1-26 of TARP (SEQ ID NO: 1), and the polypeptide does not include amino acids 38-58 of TARP (SEQ ID NO: 1).

It is believed that the presentation of peptides by MHC Class I molecules involves binding to the cleft in an MHC Class I molecule through the anchor residues of the peptide and ultimate presentation on the cell surface. Depending upon the particular anchor residues, among other things, certain peptides can bind more tightly to particular HLA molecules than others. Peptides that bind well are usually "dominant" epitopes, while those that bind less well are often "subdominant" or "cryptic" epitopes. Dominant epitopes of either self proteins or foreign proteins evoke strong tolerance or immune responses. Subdominant or cryptic epitopes generate weak responses or no responses at all. Without being bound by theory, tighter binding by dominant epitopes to HLA molecules results in their denser presentation on the cell surface, greater opportunity to react with immune cells and greater likelihood of eliciting an immune response or tolerance. MHC Class I molecules present epitopes from endogenous proteins for presentation to CTL cells. HLA A, HLA B and HLA C molecules bind peptides of about 8 to 10 amino acids in length that have particular anchoring residues. The anchoring residues recognized by an HLA Class I molecule depend upon the particular allelic form of the HLA molecule. A CD8+ T cell bears T cell receptors that recognize a specific epitope when presented by a particular HLA molecule on a cell. When a CTL precursor that has been stimulated by an antigen presenting cell to become a cytotoxic T lymphocyte contacts a cell that bears such an HLA-peptide complex, the CTL forms a conjugate with the cell and destroys it. In several examples presented herein, the polypeptides that are disclosed bind and are presented by HLA-A2.1.

In one specific, non-limiting example, an immunogenic TARP polypeptide includes one of the following amino acid sequences:

```
FLRNFSLML      (TARP-29-37, SEQ ID NO: 3)
FVFLRNFSL      (TARP-27-35, SEQ ID NO: 4)
FLANFSLML      (TARP-29-37-3A, SEQ ID NO: 5)
FLRNFSLMV,     (TARP-29-37-9V, SEQ ID NO: 6)
``` but does not include additional TARP sequences, such as a additional epitope included in SEQ ID NO: 1. In one example, the polypeptide consists of the amino acids sequence set forth as SEQ ID NO: 3, SEQ ID NO: 4, SEQ ID NO: 5, or SEQ ID NO:6, and do not include additional amino acids. In another specific, non-limiting example, the polypeptide does not include consecutive amino acids 1-26 of SEQ ID NO: 1 or consecutive amino acids 38-58 of SEQ ID NO: 1.

In another example, the polypeptide can also include heterologous sequences to TARP (e.g. amino acid sequences of at least nine amino acids in length that are not included in SEQ ID NO: 1). Thus, in several specific non-limiting examples, the immunogenic peptide is a fusion polypeptide, for example the polypeptide includes six sequential histidine residues, a β-galactosidase amino acid sequence, or a immunoglobulin amino acid sequence. The polypeptide can also be covalently linked to a carrier.

The polypeptide can optionally include repetitions of any one of SEQ ID NOs: 3-6. In one specific, non-limiting example, the polypeptide includes 2, 3, 4, 5, or up to ten repetitions of one of the sequences set forth as SEQ ID NOs: 3-6. A linker sequence can optionally be included between the repetitions.

In another embodiment, the polypeptide consists of one of the following amino acid sequences:

```
FLRNFSLML      (TARP-29-37, SEQ ID NO: 3)
FVFLRNFSL      (TARP-27-35, SEQ ID NO: 4)
FLANFSLML      (TARP-29-37-3A, SEQ ID NO: 5)
FLRNFSLMV.     (TARP-29-37-9V, SEQ ID NO: 6)
```

The immunogenic TARP polypeptides disclosed herein can also be chemically synthesized by standard methods, or can be produced recombinantly. An exemplary process for polypeptide production is described in Lu et al., *Federation of European Biochemical Societies Letters*. 429:31-35, 1998. They can also be isolated by methods including preparative chromatography and immunological separations.

In other embodiments, fusion proteins are provided comprising a first and second polypeptide moiety in which one of the protein moieties comprises an amino acid sequence of at least five amino acids identifying an epitope of TARP, such as a polypeptide described by SEQ ID NO: 9. In several examples, the TARP moiety is any one of, SEQ ID NO: 3-6. The other moiety can be a carrier protein and/or an immunogenic protein. Such fusions also are useful to evoke an immune response against TARP.

A TARP polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

Polynucleotides encoding the immunogenic TARP polypeptides disclosed herein are also provided. These polynucleotides include DNA, cDNA and RNA sequences which encode the polypeptide of interest.

A nucleic acid encoding an immunogenic TARP polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding an immunogenic TARP polypeptide include a recombinant DNA which is incorporated into a vector into an autonomously replicating plasmid or virus or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double forms of DNA.

DNA sequences encoding an immunogenic TARP polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

A polynucleotide sequences encoding an immunogenic TARP polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding an immunogenic TARP polypeptide can be inserted into an expression vector including, but not limited to, a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA can be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding an immunogenic TARP polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

Therapeutic Methods and Pharmaceutical Compositions

An immunogenic TARP polypeptide as disclosed herein can be administered to a subject in order to generate an immune response. In one embodiment, a therapeutically effective amount of an immunogenic TARP polypeptide comprising SEQ ID NO: 9, which is equivalent to amino acids 27 to 37 of SEQ ID NO: 1, wherein amino acid 31 is an R or an A and wherein amino acid 37 is an L or a V. It should be noted that in SEQ ID NO: 1, amino acid 31 is an R and amino acid 37 is an L. In specific, non-limiting examples, $X_1$ is A and $X_2$ is L, $X_1$ is A and $X_2$ is V, $X_1$ is R and $X_2$ is L, or $X_1$ is R and $X_2$ is V. The immunogenic TARP polypeptide does not include additional consecutive amino acids of TARP (SEQ ID NO: 1), such that the polypeptide does not include amino acids 1-26 of TARP (SEQ ID NO: 1), and the polypeptide does not include amino acids 38-58 of TARP (SEQ ID NO: 1).

In one specific, non-limiting example, an immunogenic TARP polypeptide is administered that includes one of the following amino acid sequences:

```
FLRNFSLML    (TARP-29-37, SEQ ID NO: 3)

FVFLRNFSL    (TARP-27-35, SEQ ID NO: 4)

FLANFSLML    (TARP-29-37-3A, SEQ ID NO: 5)

FLRNFSLMV    (TARP-29-37-9V, SEQ ID NO: 6)
``` but does not include additional TARP sequences, such as an epitope included in SEQ ID NO: 1 that is not SEQ ID NO: 3, SEQ ID NO: 4, SEQ ID NO: 5, or SEQ ID NO: 6. Thus, the polypeptide does not include amino acids 1-26 of SEQ ID NO: 1 or amino acids 38-58 of SEQ ID NO: 1. One or more of these immunogenic TARP polypeptides can be administered to a subject to treat prostate or breast cancer. Thus, one, two, three or all four of these immunogenic TARP polypeptides can be administered to a subject.

In exemplary applications, compositions are administered to a patient suffering from a disease, such as prostate or breast cancer, in an amount sufficient to raise an immune response to TARP-expressing cells. Administration induces a sufficient immune response to slow the proliferation of such cells or to inhibit their growth, or to reduce a sign or a symptom of the tumor. Amounts effective for this use will depend upon the severity of the disease, the general state of the patient's health, and the robustness of the patient's immune system. A therapeutically effective amount of the compound is that which provides either subjective relief of a symptom(s) or an objectively identifiable improvement as noted by the clinician or other qualified observer.

An immunogenic TARP polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. In one embodiment, administration is by subcutaneous or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

In one specific, non-limiting example, an immunogenic TARP polypeptide is administered in a manner to direct the immune response to a cellular response (that is, a cytotoxic T lymphocyte (CTL) response), rather than a humoral (antibody) response. A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (e.g., via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinly-seryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

In yet another embodiment, to induce a CTL response to an immunogenic TARP polypeptide, a MHC Class II-restricted T-helper epitope is added to the immunogenic TARP polypeptide to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," in Powell et al., eds., *Vaccine Design, the Subunit and Adjuvant Approach*, Plenum Press, New York, 1995).

A pharmaceutical composition including an immunogenic TARP polypeptide is thus provided. In one embodiment, the immunogenic TARP polypeptide, or fragment thereof, is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, i.e., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

An adjuvant can be included in the composition. In one embodiment, the adjuvant is a mixture of stabilizing detergents, micelle-forming agent, and oil available under the name Provax® (IDEC Pharmaceuticals, San Diego, Calif.). An adjuvant can also be an immunostimulatory nucleic acid, such as a nucleic acid including a CpG motif.

In another embodiment, a pharmaceutical composition includes a nucleic acid encoding an immunogenic TARP polypeptide or immunogenic fragment thereof. A therapeutically effective amount of the immunogenic TARP polynucleotide can be administered to a subject in order to generate an immune response. In one specific, non-limiting example, a therapeutically effective amount of the immunogenic TARP polynucleotide is administered to a subject to treat prostate cancer or breast cancer.

One approach to administration of nucleic acids is direct immunization with plasmid DNA, such as with a mammalian expression plasmid. As described above, the nucleotide sequence encoding an immunogenic TARP polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 µg encapsulated in ISCOMS™ have been found to produce Class I mediated CTL responses (Takahashi et al., *Nature* 344:873, 1990).

In another approach to using nucleic acids for immunization, an immunogenic TARP polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In one embodiment, a nucleic acid encoding an immunogenic TARP polypeptide is introduced directly into cells. For example, the nucleic acid can be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 µg/kg to about 50 mg/kg, and typically are about 0.005 mg/kg to about 5 mg/kg (see, e.g., U.S. Pat. No. 5,589,466).

In one specific, non-limiting example, a pharmaceutical composition for intravenous administration would include about 0.1 µg to 10 mg of immunogenic TARP polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Phamaceutical Sciences*, 19$^{th}$ Ed., Mack Publishing Company, Easton, Pa., 1995.

The compositions can be administered for therapeutic treatments. In therapeutic applications, a therapeutically effective amount of the composition is administered to a subject suffering from a disease, such as prostate or breast cancer. Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles can be administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In another method, antigen presenting cells (APCs), such as dendritic cells, are pulsed or co-incubated with peptides comprising an immunogenic TARP polypeptide in vitro. In one specific, non-limiting example, the antigen presenting cells can be autologous cells. A therapeutically effective amount of the antigen presenting cells can then be administered to a subject.

The immunogenic TAP polypeptide can be delivered to the dendritic cells or to dendritic cell precursors via any method known in the art, including, but not limited to, pulsing dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 µg to about 1,000 µg, or about 1 to about 100 µg of a selected immunogenic TARP polypeptide. The immunogenic TARP polypeptide can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present the immunogenic TARP polypeptide. These dendritic cells are then administered alone to a subject with a tumor that expresses TARP, such as a prostate or a breast cancer. In another embodiment, the mature dendritic cells are administered in conjunction with a chemotherapeutic agent.

Alternatively, the APCs are used to sensitize CD8 cells, such as tumor infiltrating lymphocytes (TILs) from prostate or breast tumors or peripheral blood lymphocytes (PBLs). The TILs or PBLs can be from the same subject (autologous) that is to be treated. Alternatively, the TILs or PBLs can be heterologous. However, they should at least be MHC Class-I restricted to the HLA types the subject possesses. An effective amount of the sensitized cells are then administered to the subject.

Peripheral blood mononuclear cells (PBMCs) can be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived, such as TARP (e.g. SEQ ID NO: 1).

The cells can be administered to a subject to inhibit the growth of cells of TARP expressing tumors. In these applications, a therapeutically effective amount of activated antigen presenting cells, or activated lymphocytes, are administered to a subject suffering from a disease, in an amount sufficient to raise an immune response to TARP-expressing cells. The resulting immune response is sufficient to slow the proliferation of such cells or to inhibit their growth, or to reduce a sign or a symptom of the tumor.

In a supplemental method, any of these immunotherapies is augmented by administering a cytokine, such as IL-2, IL-3, IL-6, IL-10, IL-12, IL-15, GM-CSF, interferons.

In a further method, any of these immunotherapies is augmented by administering an additional chemotherapeutic agent. In one example, this administration is sequential. Examples of such agents are alkylating agents, antimetabolites, natural products, or hormones and their antagonists. Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine). Examples of antimetabolites include folic acid analogs (such as methotrexate), pyrimidine analogs (such as 5-FU or cytarabine), and purine analogs, such as mercaptopurine or thioguanine. Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase). Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide). Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol. Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Reagents for the Detection of Cells that Express CD8 (CD8+) Cells that Specifically Bind TARP Reagents are provided herein for the detection of CD8 expressing cells that specifically bind TARP. These reagents are tetrameric MHC Class I/immunogenic TARP polypeptide complexes. These tetrameric complexes include an immunogenic TARP polypeptide that includes nine consecutive amino acids from the consensus sequence:

FVF LX$_1$NFSLMX$_2$ (SEQ ID NO: 9), wherein X$_1$ is R or A, and wherein X$_2$ is L or V.

SEQ ID NO: 9 is equivalent to amino acids 27 to 37 of SEQ ID NO: 1, wherein amino acid 31 is an R or an A and wherein amino acid 37 is an L or a V. It should be note that in SEQ ID NO: 1, amino acid 31 is an R and amino acid 37 is a L. In one specific, non-limiting example, X$_1$ is an A and X$_2$ is an L. In other specific non-limiting examples, X$_1$ is A and X$_2$ is V, X$_1$ is R and X$_2$ is L, or X$_1$ is R and X$_2$ is V.

The tetrameric complexes disclosed herein do not include additional consecutive amino acids of TARP (SEQ ID NO: 1), such that the polypeptide does not include amino acids 1-26 of TARP (SEQ ID NO: 1), and the polypeptide does not include amino acids 38-58 of TARP (SEQ ID NO: 1).

In several examples, the tetrameric complex includes an immunogenic TARP polypeptide that includes one of the following amino acid sequences:

```
FLRNFSLML      (TARP-29-37, SEQ ID NO: 3)
FVFLRNFSL      (TARP-27-35, SEQ ID NO: 4)
FLANFSLML      (TARP-29-37-3A, SEQ ID NO: 5)
FLRNFSLMV,     (TARP-29-37-9V, SEQ ID NO: 6)
``` but does not include additional TARP sequences, such as an epitope included in SEQ ID NO: 1 that is not SEQ ID NO: 3, SEQ ID NO: 4, SEQ ID NO: 5, or SEQ ID NO: 6.

Tetrameric MHC Class I/peptide complexes can be synthesized using methods well known in the art (Altmann et al., *Science* 274:94, 1996, which is herein incorporated by reference). In one specific non-limiting example, purified HLA heavy chain and β2-microglobulin (β2m) can be synthesized by means of a prokaryotic expression system. One specific, non-limiting example of an expression system of use is the pET system (R&D Systems, Minneapolis, Minn.). The heavy chain is modified by deletion of the trans-membrane and cytosolic tail and COOH-terminal addition of a sequence containing the biotin protein ligase (Bir-A) enzymatic biotinylation site. Heavy chain, β2m, and peptide are then refolded. The refolded product can be isolated by any means known in the art, and then biotinylated by Bir-A. A tetramer is then produced by contacting the biotinylated product with strepavidin.

In one embodiment, the strepavidin is labeled. Suitable labels include, but are not limited to, enzymes, magnetic beads, colloidal magnetic beads, haptens, fluorochromes, metal compounds, radioactive compounds or drugs. The enzymes that can be conjugated to strepavidin include, but are not limited to, alkaline phosphatase, peroxidase, urease and β-galactosidase. The fluorochromes that can be conjugated to the strepavidin include, but are not limited to, fluorescein isothiocyanate, tetramethylrhodamine isothiocyanate, phycoerythrin, allophycocyanins and TEXAS RED®. For additional fluorochromes that can be conjugated to strepavidin, see Haugland, R. P., *Molecular Probes: Handbook of Fluorescent Probes and Research Chemicals* (1992-1994). The metal Compounds that can be conjugated to the strepavidin include, but are not limited to, ferritin, colloidal gold, and particularly, colloidal superparamagnetic beads. The haptens that can be conjugated to the strepavidin include, but are not limited to, biotin, digoxigenin, oxazalone, and nitrophenol. The radioactive compounds that can be conjugated to strepavidin are known to the art, and include but are not limited to technetium 99m ($^{99}$Tc), $^{125}$I and amino acids comprising any radionuclides, including, but not limited to, $^{14}$C, $^{3}$H and $^{35}$S. Generally, strepavidin labeled with a fluorochrome is utilized in the methods disclosed herein.

In one embodiment, suspension of cells including T cells that specifically recognize TARP is produced, and the cells are reacted with the tetramer in suspension. In one embodiment, these reagents are used to label cells, which are then analyzed by fluorescence activated cell sorting (FACS). A machine for FACS employs a plurality of color channels, low angle and obtuse light-scattering detection channels, and impedance channels, among other more sophisticated levels of detection, to separate or sort cells. Any FACS technique can be employed as long as it is not detrimental to the detection of the desired cells. (For exemplary methods of FACS see U.S. Pat. No. 5,061,620.)

The disclosure is illustrated by the following non-limiting Examples.

EXAMPLES

To develop more effective immunotherapy for the cancer patients, it is important to find new tumor-specific antigens and establishing new vaccine strategies are important. Vasmatzis et al. (*Proc Natl Acad Sci USA* 95:300, 1998) have recently found new genes specifically expressed in human prostate by expressed sequence tag database analysis, and one of them, TCRγ alternate reading frame protein (TARP), is expressed in both prostate and breast cancer cell lines (Wolfgang et al., *Proc Natl Acad Sci USA* 97:943, 2000). This new protein, TARP, originates from epithelial cells and is located in the nucleus. Further study (Wolfgang et al., *Cancer Res* 61:8122, 2001) showed that TARP is expressed in the androgen-sensitive prostate cancer cells, LNCaP but not in androgen-independent PC3 cell line. TARP also has a role in regulating growth and gene expression in prostate cancer cell lines.

As disclosed herein, TARP is expressed in normal prostate and in most prostate cancers. Furthermore, TARP is expressed in an androgen-sensitive cell line, LNCaP, but not in the androgen-independent PC3 cell line, which suggests that TARP plays a role in prostate cancer progression (Wolfgang et al., *Cancer Res* 61:8122, 2001). Treatment of LNCaP cells with testosterone resulted in the increased expression of TARP in LNCaP cells. This protein is also expressed in a broad range of breast cancer cell lines, MCF-7, SK-BR3, BT-474, and CRL1897 (Wolfgang et al., *Proc Natl Acad Sci USA* 97:9437, 2000).

As disclosed herein, it was determined that human HLA-A2-presented epitopes derived from the TARP, and then their immunogenicities were tested in A2K$^b$ transgenic mice that have a chimeric MHC Class I molecules composed of α1 and α2 domains from HLA-A2.1 and an α3 domain from K$^b$ (Sherman et al., *Science* 258:81, 1992). Next, the immunogenicity of the peptides was enhanced by increasing their binding affinities to HLA-A2.1 molecules, and the result showed that enhanced epitopes were more immunogenic, which could increase the efficacy of a vaccine (e.g., see Berzofsky et al., *Ann. N.Y. Acad. Sci.* 690:256, 1993). As it takes a stronger signal to activate a response than to be the target of a response (Alexander et al., *J. Exp. Med.* 173:849, 1991), the natural epitope may be sufficient to allow killing of the tumor by T cells raised with the enhanced epitope. Furthermore, CD8$^+$ T cells reactive to the wild-type and enhanced epitopes were detected in prostate cancer patients. By in vitro restimulation of PBMC from prostate cancer patients with peptide-loaded dendritic cells (DC), peptide-specific CD8$^+$ T cells were detected and expanded that recognized peptide/MHC complexes and killed a human breast cancer cell line. In addition, HLA-A2.1-tetramers composed of individual peptides made in this study provide a method by which the presence of peptide-specific CD8$^+$ T cells has been detected in the patients.

Example 1

Materials and Methods

Animals. A2K$^b$ transgenic mice expressing a chimeric HLA-A2.1 transgene with the α1 and α2 domains from HLA-A2.1 and the α3 domain from H2K$^b$, to allow binding to mouse CD8, on a C57/BL6 background have been described (Sherman et al., *Science* 258:81, 1992). These mice were bred and housed in appropriate animal care facilities. All procedures with animals were conducted in accordance with the institutionally approved protocols.

Peptides. HLA-A2.1-binding peptides were synthesized on a Model Symphony peptide synthesizer (Perkin-Elmer, Boston, Mass.) using conventional f-MOC chemistry and cleaved from the resin by trifluoroacetic acid. The purity and molar concentration were analyzed by reverse-phase HPLC on a C18 column using a gradient of 0.1% trifluoroacetic acid in water and 0.1% trifluoroacetic acid in acetonitrile, and were further purified by preparative reverse phase HPLC using a similar gradient. Full-length peptides were purchased from Multiple Peptide Systems (San Diego, Calif.) at >95% purity and were single peaks by reverse-phase HPLC.

Cell lines. The T2 cell line is deficient in TAP1 and TAP2 transporter proteins and expresses low levels of HLA-A2.1. C1R-A2.1 cell line is human B lymphoblastoid cell line HMYC1R transfected with HLA-A2.1. Cells were maintained in complete medium (RPMI-1640 supplemented with 10% FCS, 100 IU penicillin, and 10 μg/ml streptomycin). RPMI 1640 and other supplements were purchased from Cellgro (Gaithersberg, Md.). For C1R-A2.1 cells, 200 μg/ml geneticin (Sigma, St. Louis, Mo.) was added into the medium. LNCaP, PC3, MCF-7, and DU145 cells were maintained in complete media. For PC3-TARP cells (Wolfgang et al., *Cancer Res* 61:8122, 2001), 200 μg/ml hygromycin B (Invitrogen, Carlsbad, Calif.) was added into the medium.

T2-binding assay. Peptide binding capacity to HLA-A2.1 molecules was measured by using the T2 cell line according to a protocol previously described (Nijman et al., *Eu. J. Immunol.* 23:1215, 1993). T2 cells (3×10$^5$/well) were incubated overnight in 96-well plates with culture medium (1:1 mixture of RPMI 1640/EHAA containing 2.5% FBS, 100 U/ml penicillin, 100 μg/ml streptomycin) with 10 μg/ml β2-microglobulin (Sigma) and different concentrations of peptide. Cells were washed twice with cold PBS containing 2% FBS and incubated for 30 minutes at 4° C. with anti-HLA-A2.1 BB7.2 mAb (1/80 dilution from hybridoma supernatant). After washing, cells were stained with FITC-labeled goat anti-mouse Ig (PharMingen, San Diego, Calif.) and the level of HLA-A2.1 expression was measured by flow cytometry. HLA-A2.1 expression was quantified as fluorescence index (FI) according to the formula: FI=(mean fluorescence intensity with peptide-mean fluorescence intensity without peptide)/mean fluorescence intensity without peptide.

Immunizations. A2K$^b$ transgenic mice were immunized with syngeneic peptide-loaded dendritic cells (DC), plasmid DNA expressing TARP, or the mixture of peptide and cytokine in incomplete Freund's adjuvant (IFA). For DC immunization, DC were pulsed with 10 μM peptide in serum-free RPMI for 2 hours at 37° C., and then mice were immunized subcutaneously (s.c.) with 1-3×10$^5$ DC without washing. DC were prepared from bone marrow as previously described (Celluzzi et al. *J. Exp. Med.* 183:283, 1996). Alternatively, mice were immunized intramuscularly with 100 μg plasmid DNA, pcDNA5/FRT/TARP, generated by inserting the TARP DNA into the pcDNA5/RFT (Invitrogen, Carlsbad, Calif.) vector. Mice were also immunized subcutaneously (s.c.) in the base of the tail with 100 μl of an emulsion containing 1:1 IFA and PBS with antigens and cytokines (50 nmol CTL epitope, 50 nmol HBV core 128-140 helper epitope, 3 μg of IL-12, and 5 μg of granulocyte macrophage colony stimulating factor (GM-CSF). IFA and cytokines were purchased from Sigma and Peptotech (Rocky Hill, N.J.), respectively.

In vitro human CD8+ T cell priming with DC. Elutriated monocytes and lymphocytes were obtained from HLA-A2.1-positive patients or normal donors. To prepare DC, monocytes were cultured at $10^6$ cells/ml in complete medium containing human IL-4 (1000 units/ml) and human GM-CSF (1000 units/ml). On day 2 and 4, half of the media was exchanged. To mature the DC, CD40 ligand trimer (Immunex, Seattle, Wash.) was added at 1 μg/ml on day 4 or 5, and then further cultured for 2 or 3 days. Cells were harvested on day 7, and then pulsed with 10 μM of peptides for 2 hours before γ-irradiation. $1 \times 10^5$ peptide-pulsed DC and $2 \times 10^6$ autologous CD8+ T cells were mixed and cultured in 24-well plates. 10 units/ml IL-2 was added on day 2 during restimulation. Cells were restimulated every 7-9 days approximately 4-7 cycles.

CTL assay. For murine CTL, CD8+ T cells from the immunized mice were restimulated with peptide-loaded splenocytes for one week as previously described (Oh et al., *J Immunol* 170:2523, 2003), and then applied to 5 hour $^{51}$Cr release assays. Target cells were labeled with $^{51}$Cr first and washed twice. Cells were then pulsed with peptides for 2 hours and used as target cells without further washing. For human CTL, target cells were also labeled with $^{51}$Cr first, and then loaded with peptides. In the CTL assay against human tumor cells, target cells were incubated in the complete medium containing 1000 units/ml IFN-γ for 72 hours. The mean of triplicate samples was calculated, and the percentage of specific lysis was determined using the following formula: Percentage of specific lysis=100×[(experimental $^{51}$Cr release−control $^{51}$Cr release)/(maximum $^{51}$Cr release−control $^{51}$Cr release)]. The maximum release refers to counts from targets in 2.5% Triton X-100.

HLA-A2.1 tetramers. Tetrameric MHC Class I/peptide complexes were synthesized as described (Altmann et al., *Science* 274:94, 1996). Briefly, purified HLA heavy chain and β2-microglobulin (β2m) were synthesized by means of a prokaryotic expression system (pET; R&D Systems, Minneapolis, Minn.). The heavy chain was modified by deletion of the trans-membrane and cytosolic tail and COOH-terminal addition of a sequence containing the Bir-A enzymatic biotinylation site. Heavy chain, β2m, and peptide were refolded by dilution. The refolded product was isolated by FPLC and then biotinylated by Bir-A in the presence of biotin, adenosine 5'-triphosphate, and $Mg^{++}$ (all from Sigma). Streptavidin-PE conjugate (PharMingen) was added in 1:4 molar ratio.

Antibody and flow cytometry. FITC-labeled anti-mouse CD8 (53-6.7), CD11c, CD80 (B7-1), CD54 (ICAM-1), anti-human CD8 (RPA-T8), CD14 (5E2), CD80 (B7-1), and CD86 (B7-2) were used for staining of cell surface molecules. For intracellular IFN-γ staining, cells were stained by following the manufacturer's protocol. All Abs and reagents were purchased from PharMingen. For flow cytometric analysis of cell surface, $5 \times 10^5$ cells were washed and resuspended in PBS containing 0.2% BSA and 0.1% sodium azide. Cells were incubated on ice with the appropriate antibody for 30 minutes and then washed. Samples were analyzed on a FACScan (BD Biosciences, Mountain View, Calif.). Background staining was assessed by use of an isotype control antibody. For tetramer staining, cells were incubated with FITC-labeled anti-CD8 for 10 minutes, and then stained with tetramers.

Example 2

HLA-A2.1-Restricted Epitope Prediction and Wild-Type Peptide Binding Affinity to HLA-A2.1 Molecules Fifty-eight amino acid residues in the TARP protein were previously characterized (Wolfgang et al., *Proc Natl Acad Sci USA* 97:9437, 2000) (FIG. 1A). To determine HLA-A2.1 epitopes from the TARP, four different wild-type peptides were first predicted based on the anchor residues (FIG. 1B) and their binding affinities to HLA-A2.1 molecules were measured by the T2-binding assay. As shown in FIG. 1C, only two wild-type peptides, TARP-29-37 and TARP-27-35, showed measurable binding capacity to HLA-A2.1 molecules. Although both peptides overlap by seven residues, TARP-27-35 had almost a ten-fold higher binding affinity to HLA-A2.1 molecules than TARP-29-37. Neither TARP-2-9 nor TARP-22-30 showed any measurable binding affinity to HLA-A2.1 molecules.

The theoretical half-life of peptide binding to HLA-A2.1 molecules was also predicted by running the software program for peptide motif search (Parker et al., *J. Immunol.* 152:163, 1994), and the results were consistent with the data in FIG. 1C.

TARP is composed of 58 amino acid residues and contains several hydrophobic amino acids including five leucines, but data from the T2-binding assay showed that only two wild-type peptides (TARP-29-37, SEQ ID NO: 3 and TARP-27-35, SEQ ID NO: 4) had a measurable binding affinity to HLA-A2.1 molecules. Seven out of nine amino acids in both wild-type peptides overlap. Moreover, they both share two amino acids at same positions, Phe at position 1 and Leu at position 9, although the amino acid at position 1 is not a primary anchor residue. However, TARP-27-35 (SEQ ID NO: 4) showed a better binding affinity than TARP-29-37 (SEQ ID NO: 3). Without being bound by theory, this is probably because of other amino acids in non-anchor positions, such as Phe at position 3 in TARP-27-35 (SEQ ID NO: 4). Although the other two wild-type peptides, TARP-2-9 (SEQ ID NO: 7) and TARP-22-30 (SEQ ID NO: 8), possess Leu at position 9 and Met or Leu at position 2, respectively, neither TARP-2-9 (SEQ ID NO: 7) nor TARP-22-30 (SEQ ID NO: 8) showed a measurable binding affinity to HLA-A2.1 molecules. Neither TARP-27-35 (SEQ ID NO: 4) and TARP-29-37 (SEQ ID NO: 3) have any residues known to be associated with poor HLA-A2.1 binding at the secondary anchor positions. Without being bound by theory, this suggests that primary anchor residues alone are not sufficient to determine the binding affinity of peptides (Ruppert et al., *Cell* 74:929, 1993; Rammensee et al., *Immunogenetics* 41:178, 1994), and/or the large number of Pro residues affected the conformation of TARP-2-9 (SEQ ID NO: 7) and that the Glu at position 3 may have interfered with binding of TARP-22-30 (SEQ ID NO: 8). Although epitope enhancement by replacing the Glu in TARP-22-30 (SEQ ID NO: 8) might have improved binding, if the wild-type binding is too weak to serve as a good target for CTL raised against the enhanced-peptide, it is unlikely that such an enhanced-peptide would be useful.

Example 3

Wild-Type HLA-A2.1 Epitopes Induce Peptide-Specific CD8+ T Cell Responses in $A2K^b$ Transgenic Mice To verify whether those two wild-type peptides predicted in FIG. 1B are immunogenic or not, $A2K^b$ transgenic mice were immunized with either peptide-pulsed DC or plasmid DNA expressing the TARP. As shown in FIGS. 2A and 2B, both peptides could induce peptide-specific CD8+ T cell responses in the mice immunized by either immunization protocol, but responses were higher after peptide-pulsed DC immunization. Compared to TARP-27-35, however, TARP-29-37 resulted in lower peptide-specific CD8+ T cell responses, indicating that binding affinity of peptide to MHC molecules is a major factor that regulates the induction of CD8+ T cell responses. The number of IFN-γ-producing CD8+ T cells was also measured by intracellular staining. Consistent with the CTL data, a greater number of CD8+ T cells, 2.1% of total CD8+ T cells, was obtained from the mice immunized with DC pulsed with TARP-27-35 than the mice immunized with TARP-29-37-pulsed DC. However, the data indicated that mice immunized with TARP-29-37 pulsed-DC also had a significant number of CD8+ T cells producing IFN-γ. The number of IFN-γ-producing CD8+ T cells was also measured in mice immunized with DNA plasmid and the data were consistent with the data in FIG. 2C.

Data from the DNA immunization experiments indicate that the murine antigen processing system is not a limitation for production of peptides presented by human Class I molecules. Moreover, the data suggests that such HLA-transgenic mice can be used for the study of peptides recognized by CD8+ T cells specific for HLA-A2/peptide complex. Peptide/HLA-A2 complexes recognized by murine T cells might be different from those recognized by human T cells (explaining why the cross-reactivity of CD8+ T cells from mouse and human was not exactly the same). It is theoretically possible that those species differences may be due to different TCR repertoires. However, the data showed that both wild-type and enhanced epitopes resulted in the induction of peptide-specific CD8 T cells in HLA-A2 transgenic mice, and therefore these mice can be used as good predictors of human T cell epitopes.

Example 4

Amino Acid Substitutions in the Wild-Type Peptides Result in Increased Binding Affinity to HLA-A2 Molecules (Epitope-Enhancement)

Figure 3C:
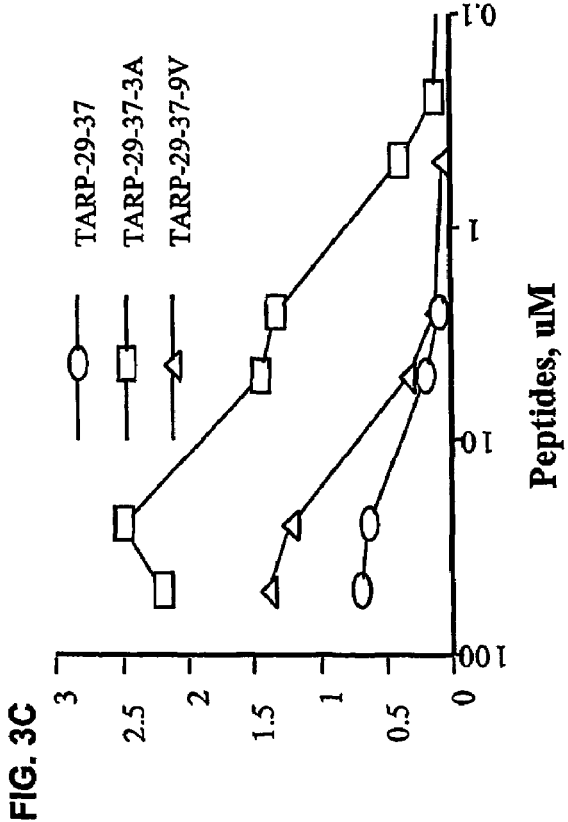
Figure 3B:
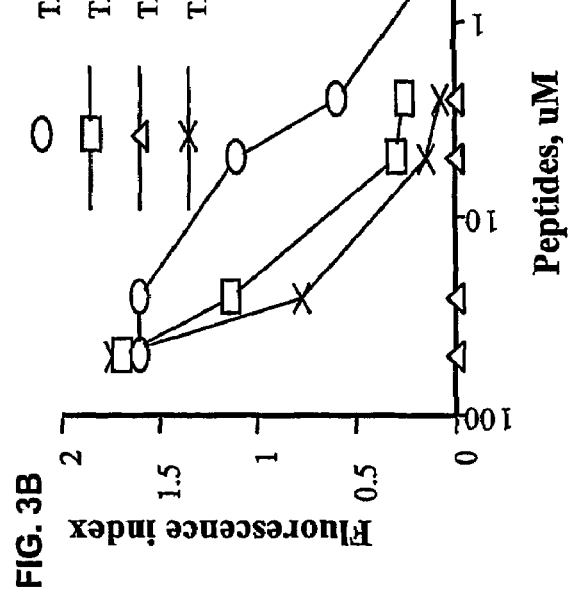

Binding affinity of peptide to MHC Class I molecules is a major factor determining the immunogenicity of peptide epitopes. To enhance the binding affinity of wild-type epitopes, TARP-29-37 (SEQ ID NO: 3) and TARP-27-35 (SEQ ID NO: 4), amino acids in the peptides were substituted with others. For TARP-29-37, Arg at position 3 and Leu at position 9 were substituted with Ala (TARP-29-37-3A, SEQ ID NO: 5) and Val (TARP-29-37-9V, SEQ ID NO: 5), respectively (FIG. 3A). As shown in FIG. 3C, substitution at position 3 with Ala in TARP-29-37 resulted in the greatest increase in the binding affinity of the peptide. The binding affinity of TARP-29-37-3A was not less than that of the positive control peptide, FMP (flu matrix peptide) (Gotch et al., *Nature* 326:881, 1987). Although TARP-29-37-9V (SEQ ID NO: 6) showed a lower binding affinity to HLA-A2.1 than TARP-29-37-3A (SEQ ID NO: 5) did, substitution of Leu at position 9 with Val did enhance the binding affinity of wild-type peptide, TARP-29-37 (SEQ ID NO: 3). In addition to TARP-29-37 (SEQ ID NO: 3), it was tried to improve the binding affinity of TARP-27-35 (SEQ ID NO: 4) by substitution of amino acids in position 2, 3, and 9 with Leu, Ala, and Val, respectively, but there was no significant enhancement in binding affinity to HLA-A2.1 molecules. In contrast to the situation with TARP-29-37, substitution with Ala at position 3 in TARP-27-35 (SEQ ID NO: 4, see FIG. 3B) resulted in no binding of the peptide to HLA-A2.1 molecules, suggesting that the peptide binding affinity to MHC molecules was not simply determined by a single amino acid, but influenced by other amino acids in the epitope. Two other substitutions at position 2 of TARP-27-35 (SEQ ID NO: 4) with Leu (TARP-27-35-2L) and at position 9 of TARP-27-35 (SEQ ID NO: 4) with Val (TARP-27-35-9V) did not alter the binding affinity of the wild-type peptide, TARP-27-35 (SEQ ID NO: 4) (FIG. 3B).

As disclosed herein, when a wild-type peptide does bind, but perhaps not optimally, one strategy to improve the usage of self-peptides such as TARP-29-37 (SEQ ID NO: 3) and TARP-27-35 (SEQ ID NO: 4) by developing enhanced-epitopes that are potentially more immunogenic. Substitution of Arg at position 3 with Ala in TARP-29-37 (SEQ ID NO: 3) greatly improved the peptide binding affinity to the HLA-A2.1 molecules. This could be explained by an adverse effect of Arg at position 3 reducing the peptide binding affinity to HLA-A2.1 as well as the stability of the peptide/MHC complexes. Substitution of Leu at position 9 with Val in TARP-29-37 (SEQ ID NO: 3) also resulted in the increased binding affinity of the peptide.

Substitutions were also made in TARP-27-35 (SEQ ID NO: 4) by substitutions for Val at position 2, Phe at position 3, and Leu at position 9 with Leu, Ala, and Val, respectively, but those substitutions did not improve the binding affinity of TARP-27-35 (SEQ ID NO: 4). Amino acid residues associated with poor binding to HLA-A2.1 are Asp, Glu, and Pro at position 1; Asp and Glu at position 3; Arg, Lys, His, and Ala at position 4; Pro at position 5; Arg, Lys, and His at position 7; Asp, Glu, Arg, Lys, and His at position 8; and Arg, Lys, and His at position 9 (Ruppert et al., *Cell* 74:929, 1993; Rammensee et al., *Immunogenetics* 41:178, 1995). Both TARP-27-35 and TARP-29-37 do not have any residue known to be associated with poor HLA-A2 binding at the secondary anchor positions. In contrast, as noted, the low binding affinity of the wild-type peptides, $TARP_{2-9}$ and TARP-22-30, is probably due to the Pro at position 5 and Glu at position 3, respectively.

Example 5

Immunogenicity of the Enhanced Epitopes and CD8+ T Cell Responses to the Wild-Type Peptides Both TARP-29-37-3A (SEQ ID NO: 5) and TARP-29-37-9V (SEQ ID NO: 6) showed better binding affinity to HLA-A2.1 molecules than the wild-type, TARP-29-37 (SEQ ID NO: 3) (see FIGS. 1 and 3). To test the immunogenicities and recognition of the wild-type peptide by CD8+ T cells induced with the enhanced epitopes, mice were immunized with those peptides. As shown in FIG. 4A, both TARP-29-37-3A (SEQ ID NO: 5) and TARP-29-37-9V (SEQ ID NO: 6) induced almost two-fold higher frequencies of CD8+ T cells specific for individual peptides compared to the wild-type, TARP-29-37 (SEQ ID NO: 3). Another wild-type epitope, TARP-27-35 (SEQ ID NO: 4) also induced a higher frequency of CD8+ CTL specific for the peptide (but these CD8+ CTLs did not recognize TARP-29-37 (SEQ ID NO: 3) and the epitope-enhanced peptides, see FIG. 4B).

In a cross-reactivity analysis (see FIGS. 4B-D), CD8+ CTL induced with both enhanced epitopes lysed target cells pulsed with TARP-29-37 (SEQ ID NO: 3), suggesting that the TCRs of those CTL recognize the wild-type peptide (TARP-29-37)-MHC Class I complex to some extent. The immunogenicity of the enhanced versus wild-type TARP-29-37 peptides shown in FIG. 4A correlated with the peptide affinity for HLA-A2.1 (shown in FIG. 3). However, CD8+ CTL induced with TARP-29-37-3A (SEQ ID NO: 5) recognized TARP-29-37-3A/MHC complex better than other peptide/MHC Class I complexes. In contrast, CTL raised against TARP-29-37-9V (SEQ ID NO: 6) were slightly more potent in killing targets pulsed with wild-type TARP-29-37 (SEQ ID NO: 3), suggesting that they could be more effective against tumor cells expressing the natural antigen (FIG. 4B). When compared quantitatively (FIGS. 4C and 4D), TARP-29-37-9V (SEQ ID NO: 6) was the most immunogenic of the peptides in inducing CTLs specific for the wild-type sequence. Thus, TARP-29-37-9V (SEQ ID NO: 6) could be the most potent of the immunogens for inducing CTLs against tumor cells expressing the natural antigen.

Interestingly, CD8+ CTL induced with TARP-29-37-9V (SEQ ID NO: 6) could also kill target cells pulsed with TARP-27-35 (SEQ ID NO: 4). In contrast, CTL induced with TARP-29-37-3A (SEQ ID NO: 5) did not kill target cells pulsed with TARP-27-35 (SEQ ID NO: 4), suggesting that CD8+ T cells induced with TARP-29-37-9V (SEQ ID NO: 6) have broader cross-reactivity to wild-type peptide/MHC complexes than CD8+ T cells induced with TARP-29-37-3A (SEQ ID NO: 5). This suggests that TARP-29-37-9V (SEQ ID NO: 6) can be used to induce CD8+ T cells that could recognize antigen expressed on tumor cells.

Example 6

Human CD8+ T Cells Raised In Vitro Lyse Peptide-Pulsed Target Cells

TARP expression is particularly high in the prostate of prostate cancer patients, and human prostate cancer cell lines also express high level of TARP (e.g., see Essand et al., *Proc Natl Acad Sci USA* 96:9287, 1999; Wolfgang et al., *Proc Natl Acad Sci USA* 97:9437, 2000; Wolfgang et al., *Cancer Res* 61:8122, 2001).

Figure 5A:
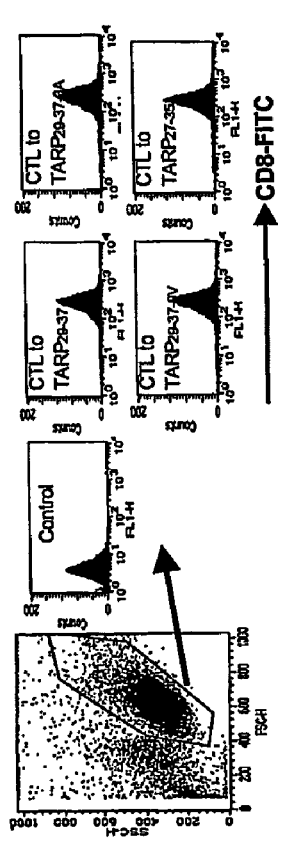
FIGS. 5A-B are plots and a line graph showing that human CD8$^+$ CTL raised by in vitro stimulation kill peptide-loaded target cells. CD8$^+$ T cells from a prostate cancer patient were restimulated with 10 µM peptide-pulsed autologous dendritic cells (DCs). DCs were derived from the culture of autologous monocytes in granulocyte macrophage colony-stimulating factor and interleukin 4. To mature the DCs, CD40 ligand (2 µg/ml) was added on day 4, and then cells were further cultured for 2-3 days before loading peptides. After several cycles of in vitro restimulation, CD8$^+$ T cells were used as effector cells. For the results show in FIG. 5A, cells were stained with anti-CD8α or isotype control antibody. For the results shown in FIG. 5B, in 5-hour $^{51}$Cr release assay, C1R-A2.1 cells were labeled with $^{51}$Cr and then pulsed with peptides. Closed and open circles represent target cells pulsed with and without peptides, respectively. Data are representative of two repeated experiments with similar results.

To test for the presence of peptide-specific CD8+ T cells (FIG. 5A) in an HLA-A2.1-positive prostate cancer patient, CD8+ T cells from the leukapheresis of the patient donor were restimulated with peptide-pulsed autologous DC in several cycles. During the in vitro restimulation, peptide-specific CD8+ T cells were first observed from the CD8+ T cell culture restimulated with TARP-29-37-3A (SEQ ID NO: 5) pulsed-DC, and then TARP-29-37-9V (SEQ ID NO: 6) specific CD8+ T cells were raised. During the in vitro restimulation, peptide-specific CD8+ T cells were detected after only four cycles of restimulation with TARP-29-37-3A (SEQ ID NO: 5)-pulsed DCs, whereas TARP-29-37-9V (SEQ ID NO: 6)-specific CD8+ T cells required at least five cycles.

Figure 5B:
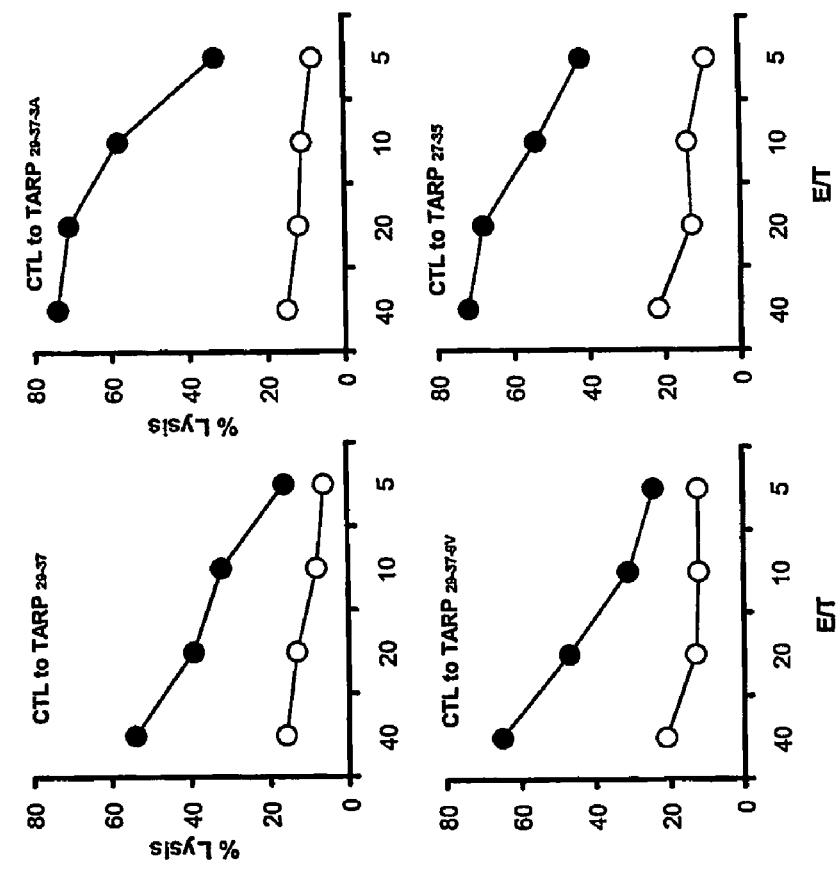

For both wild-type peptides (TARP-29-37 (SEQ ID NO: 3) and TARP-27-35 (SEQ ID NO: 4), CD8+ CTL required at least 6 cycles of in vitro restimulation to be detected. Cytolytic activity of those CD8+ CTL raised with individual peptides was tested against peptide-pulsed C1R-A2.1 target cells. All four CD8+ CTL could lyse peptide-pulsed target cells specifically, as shown in FIG. 5B. However, CD8+ CTL raised with TARP-29-37-3A (SEQ ID NO: 5) and TARP-27-35 (SEQ ID NO: 4) resulted in higher levels of cytolytic activity against the corresponding peptides compared to CD8+ CTL raised with TARP-29-37 (SEQ ID NO: 3) and TARP-29-37-9V (SEQ ID NO: 6).

Example 7

Human CD8+ T Cells Raised Against TARP-29-37-9V (SEQ ID NO: 6), but not TARP-29-37-3A (SEQ ID NO: 5), Recognize the MHC Complex with the Wild-Type Peptide, TARP-29-37 (SEQ ID NO: 3)

Figures 6A, 6B:
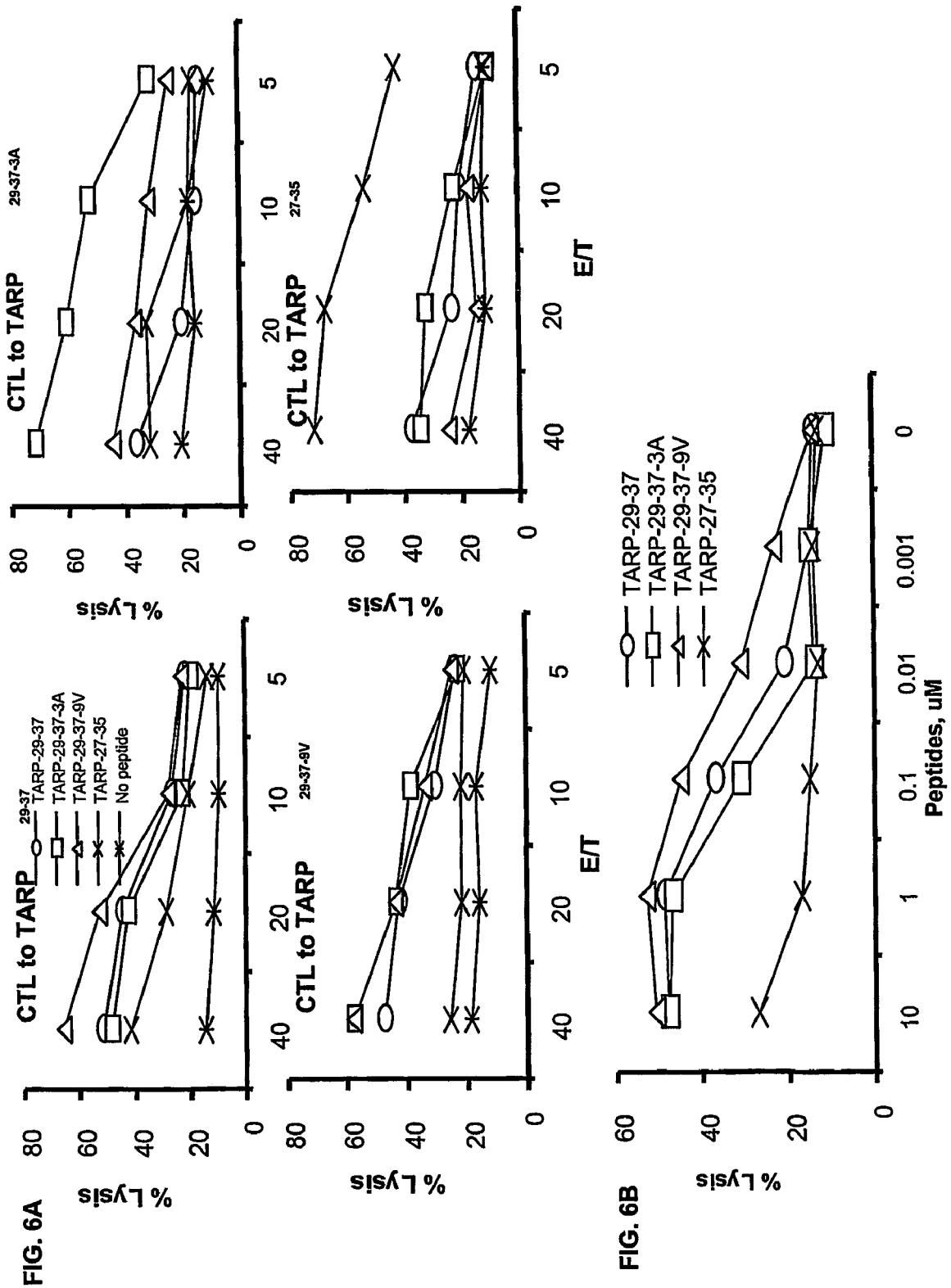
FIGS. 6A-B are two sets of line graphs showing cross-reactivity of human CD8$^+$ CTL to different HLA-A2 peptide epitopes. Human CD8$^+$ CTL were raised as described in the description above for FIG. 5. For the results shown in FIG. 6A, in a 5-hour $^{51}$CR release assay, C1R-A2.01 cells were labeled with $^{51}$Cr and then pulsed with 10 µM peptides. For the results shown in FIG. 6B, specificity and avidity of CD8$^+$ T cells specific for TARP29-37-9V to other peptides were tested by using target cells pulsed with different concentrations of the indicated peptides. Data are representative of two repeated experiments with similar results.

As disclosed herein, murine CD8+ CTL induced by the enhanced epitopes lysed wild-type peptide-pulsed target cells (FIG. 4) and human CD8+ CTL raised against individual peptides lysed target cells pulsed with the corresponding peptides (FIG. 5). However, it is important to know whether human CD8+ CTL raised against enhanced epitopes could lyse target cells pulsed with wild-type peptide expected to be presented on tumor cells. To address this question, cytolytic activity of individual CD8+ CTL was measured against target cells pulsed with different peptides. As shown in FIG. 6A, human CD8+ CTL raised with TARP-29-37 (SEQ ID NO: 3) could recognize and lyse target cells pulsed with the wild-type as well as the two enhanced epitopes (TARP-29-37-3A (SEQ ID NO: 5) and TARP-29-37-9V (SEQ ID NO: 6). However, TARP-29-37-3A-(SEQ ID NO: 5) specific CD8+ T cells poorly recognized the wild-type and TARP-29-37-9V (SEQ ID NO: 6), although they recognized TARP-29-37-3A (SEQ ID NO: 5) very well.

Unlike CD8+ T cells raised with TARP-29-37-3A (SEQ ID NO: 5), CD8+ T cells specific for TARP-29-37-9V (SEQ ID NO: 6) could recognize both wild-type and TARP-29-37-3A comparably. Data from FIG. 6 confirm that CD8+ T cells raised with TARP-29-37-9V (SEQ ID NO: 6), but not 29-37-3A (SEQ ID NO: 5), could recognize both wild-type and enhanced epitope/MHC complex. CD8+ CTL induced with TARP-27-35 (SEQ ID NO: 4) recognized TARP-27-35 (SEQ ID NO: 4)/MHC complex, but poorly recognized other peptide/MHC complexes tested. The data also showed that all three CTL raised with TARP-29-37 (SEQ ID NO: 3), TARP-29-37-3A (SEQ ID NO: 5), and TARP-29-37-9V (SEQ ID NO: 6) could recognize TARP-27-35 (SEQ ID NO: 4) to some extent, possibly due to the 7-residue overlap between them.

The avidity of CD8+ CTLs specific for TARP-29-37-9V to different peptides was measured (FIG. 6B). CTLs for TARP-29-37-9V (SEQ ID NO: 6) recognized TARP-29-37-9V (SEQ ID NO: 6) at the 0.001 µM level. Although the avidity of these CTLs for wild-type TARP-29-37 (SEQ ID NO: 3) was lower, they could recognize the wild-type as well as TARP-29-37-3A (SEQ ID NO: 5) with only slightly lower avidity. However, these CTLs did not recognize TARP-27-35 (SEQ ID NO: 4) at <10 µM concentration.

Example 8

Human CD8+ T Cells Raised Against TARP-29-37-9V and TARP-27-35 Kill TARP-Expressing Tumor Cells As disclosed herein, CD8+ T cells specific for individual peptides lyse the target cells pulsed with corresponding peptides. In addition, TARP-29-37 (SEQ ID NO: 3)- and TARP-29-37-9V (SEQ ID NO: 6)-specific CD8+ T cells killed the wild-type peptide (TARP-29-37, SEQ ID NO: 5)-pulsed target cells efficiently. CD8+ T cells specific for TARP-27-35 (SEQ ID NO: 4) also lysed TARP-27-35-pulsed target cells. To test whether those CTL could kill human tumor cells that endogenously express TARP, a CTL assay was performed against tumor cell lines that express both HLA-A2.1 and TARP, and the data are shown in FIG. 7A. At a 50:1 E/T ratio, all CD8+ T cells could kill the breast cancer line, MCF-7, but showed marginal (10-12%) lytic activity against the prostate cancer cell line, LNCaP. Before CTL assay, all target cells were cultured in medium containing IFN-γ, and the expression levels of HLA-A2.1 before and after IFN-γ-treatment were measured (FIG. 7B). As expected from the CTL assay, LNCaP cells express an extremely low level of HLA-A2.1 and the level of HLA-A2.1 was not much increased by the culture of the cells in medium containing IFN-γ. In contrast, the level of HLA-A2.1 in MCF-7 was higher to start and greatly enhanced by IFN-γ. Both control cell lines, DU-145 and PC3-TARP did not express HLA-A2.1. Similar to the HLA-A2 expression levels, data from real-time PCR showed that IFN-γ did not increase the expression level of TARP in LNCaP cells but slightly and variably increased the level in MCF-7 cells. Of four different CD8+ CTL, CD8+ T cells specific for either TARP-29-37-9V (SEQ ID NO: 6) or TARP-27-35 (SEQ ID NO: 4) showed higher lytic activity against MCF-7 than CD8+ CTL raised with TARP-29-37 (SEQ ID NO: 3) and TARP-29-37-3A (SEQ ID NO: 5). Although CD8+ CTL specific for TARP-29-37-3A (SEQ ID NO: 5) showed less lytic activity to MCF-7 at a 50:1 E/T ratio than the other three CD8+ CTL did, comparable range of lytic activity against MCF-7 cells was observed at high E/T ratio (100:1 E/T ratio).

CD8+ CTLs typically express clonally distributed TCRs that possess exquisite specificity for a particular MHC/peptide complex. In both mice and humans, however, CD8+ T cells raised with individual peptides can recognize a range of cross-reactive peptide/MHC complexes, depending on the individual CD8+ CTLs and peptides. The cross-reactivity observed in this study not only among variants of one peptide but between the two wild-type peptides could be explained by the fact that the two wild-type peptides overlap by seven amino acid residues. A number of recent studies have shown degenerate recognition of MHC/peptide complexes by individual TCRs: examples range from T-cell recognition of dissimilar peptides presented by the same MHC molecules to recognition of identical peptides bound to different MHC molecules. For example, CD8+ T cells specific for one peptide of polyoma virus recognize another epitope that has no sequence homology. However, those CD8+ T cells require a much higher concentration of the alternative peptide for recognition.

In the cross-reactivity test for human and CD8+ T cells, CD8+ T cells specific for TARP-29-37 (SEQ ID NO: 3) could recognize all four peptide/MHC complexes. However, CD8+ T cells specific for TARP-27-35 or TARP-29-37-3A (SEQ ID NO: 5) did not recognize other peptides as much as they did the immunogens. Of the enhanced peptides, only CTLs specific for TARP-29-37-9V (SEQ ID NO: 6) could recognize the wild-type peptide, TARP-29-37 (SEQ ID NO: 3), to a similar degree to the immunogen. In consideration of choosing peptides for immunotherapy, either TARP-29-37-9V (SEQ ID NO: 6) or TARP-27-35 (SEQ ID NO: 4) will likely be more potent than the other two peptides. Although TARP-29-37-3A (SEQ ID NO: 5) showed the highest binding affinity and resulted in high CD8+ T cell responses in transgenic mice (FIG. 4D), CD8+ T cells specific for this peptide did not recognize wild-type peptide very well in the human and showed weak cross-reactivity to wild-type peptide in the mice. For the tumor killing assay, CD8+ T cells specific for TARP-29-37-3A (SEQ ID NO: 5) showed a significant range of specific lysis only at a 100:1 E:T ratio. At a 50:1 E:T ratio, CD8+ T cells specific for TARP-29-37-3A (SEQ ID NO: 5) showed a much lower lytic activity against tumor cells than CTLs to TARP-29-37-9V (SEQ ID NO: 6). In contrast, TARP-29-37-9V (SEQ ID NO: 6) induced a higher level of CD8+ T cell responses than TARP-29-37, and CD8+ T cells specific for TARP-29-37-9V (SEQ ID NO: 6) could recognize the wild-type peptide, TARP-29-37 (SEQ ID NO: 3), and could kill human tumor cells. CD8+ T cells specific for TARP-27-35 (SEQ ID NO: 4) could kill human tumor cells as well.

Example 9

Figure 8:
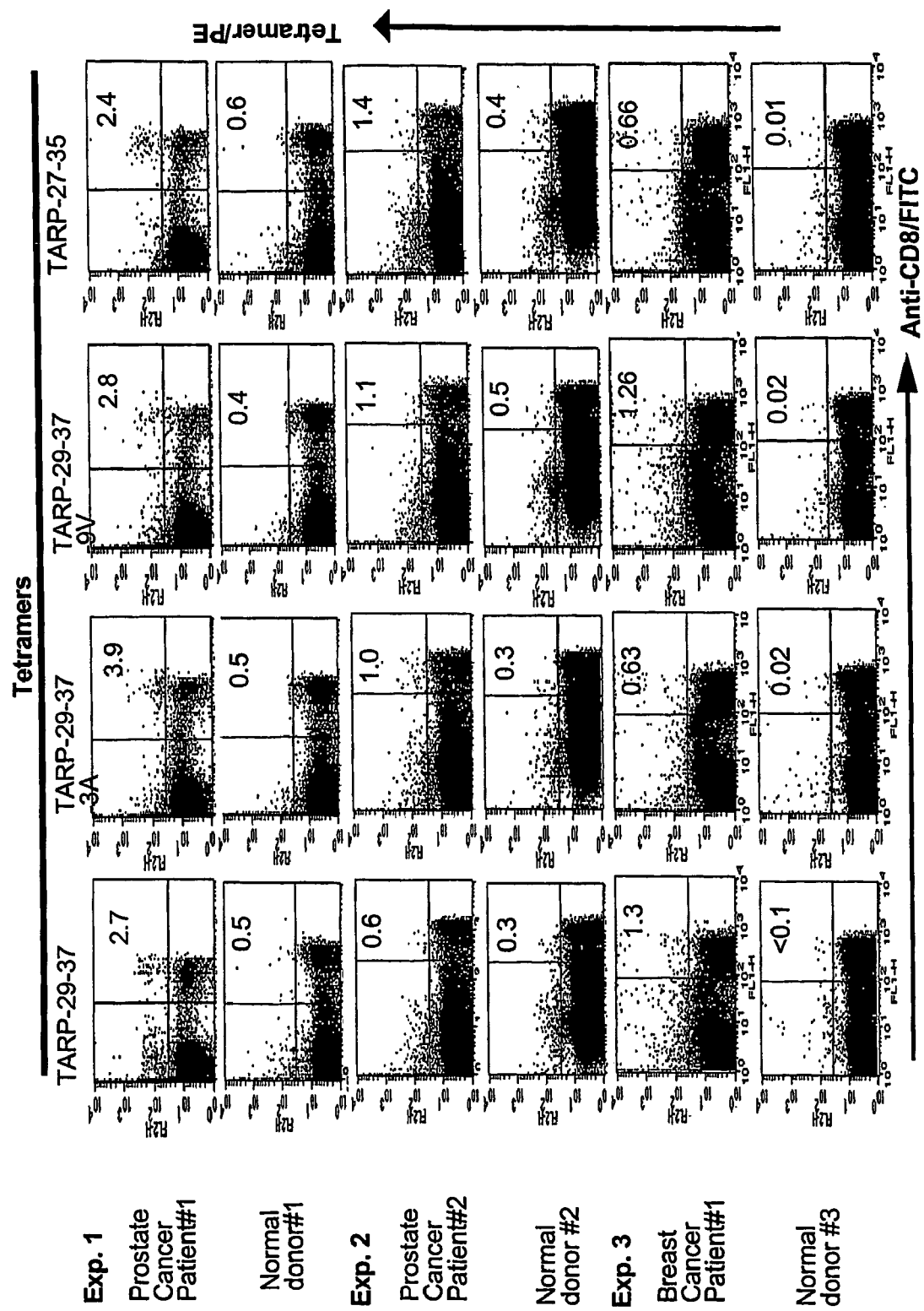
FIG. 8 is a diagram including a set of plots from two experiments showing HLA-A2-tetramers composed of wild-type and enhanced-epitopes recognize peptide-specific CD8$^+$ T cells in human blood samples. Tetramers of HLA-A2 and peptide were made as described in the Example section. Peripheral blood mononuclear cells from breast and prostate cancer patients and normal donors were stained with anti-CD8-FITC and tetramer-PE and then analyzed by flow cytometry. A normal donor was tested simultaneously with each patient as a negative control. Data are representative of two repeated experiments with similar results.

HLA-A2.1-Tetramers with Individual Peptides Recognize Peptide-Specific CD8+ T Cells in the Patients Data shown in FIGS. 5 to 7 indicate that prostate cancer patients have CD8+ T cells that recognize individual peptide and HLA-A2.1 complexes. This is compatible with previously published data that the expression level of TARP is significantly elevated in the prostate of prostate cancer patients (Wolfgang et al., *Proc Natl Acad Sci USA* 97:9437, 2000). To determine whether those CD8+ T cells exist only in the patient, CD8+ T cells from normal donors were repeatedly stimulated with peptide-pulsed autologous DC, but CD8+ T cells were not raised that were specific for any of the tested peptides in this experiment. To examine the frequency of peptide specific CD8+ T cells in the prostate cancer patients, tetramers were made that were composed of individual peptides bound to HLA-A2.1. PBMC were stained with anti-CD8 and these tetramers. As shown in FIG. 8, all four tetramers detected CD8+ T cells from the prostate cancer patients, but not the normal donors, suggesting that those tetramers could be used for detection of peptide-specific CD8+ T cells, such as for diagnostic purposes. The results also indicate that the presence of prostate cancer is sufficient to induce CD8+ T cells specific for these epitopes to a fairly high frequency (as 0.6% to 3% of total CD8+ T cells in the patients' PBMC). The frequency of peptide-specific CD8+ T cells could be dependent on the stage of tumor in the patients.

In each case, the frequency of tetramer-positive cells was substantially higher in the patient than in a normal donor tested concurrently. TCR repertoire usage was analyzed in peptide-specific CD8+ T cells from prostate cancer patient 1, and the data indicate that CD8+ T cells specific for individual peptides use a variety of TCR repertoires: Vβ3 (4.8%), Vβ5 (19.5%), Vβ8 (38%), Vβ12 (5.4%), and Vβ23 (28.6%) for TARP-27-35-specific CD8+ T cells; Vβ3 (13.1%), Vβ5 (12.9%), Vβ8 (19.2%), Vβ12 (3.4%), and Vβ23 (23.6%) for TARP29-37-specific CD8+ T cells; Vβ3 (7.7%), Vβ5 (7.4%), Vβ8 (16.7%), Vβ12 (16.8%), and Vβ23 (19.3%) for TARP29-37-3A-specific CD8+ T cells; and Vβ3 (3.4%), Vβ5 (26.7%) Vβ8 (30%), Vβ12 (2.4%), and Vβ23 (23%) for TARP29-37-9V-specific CD8+ T cells. In a phenotype analysis, about 40-60% and 19-40% of peptide-specific CD8+ T cells in the patients expressed CD45RA and CD45RO, respectively. However, <2% of CD8+ T cells express CCR7, and the majority of cells were CD62L$^{low}$, suggesting that most of the peptide-specific CD8+ T cells are activated forms and that the majority of the memory cells are not central memory CD8+ T cells.

Thus, the peptides disclosed herein, specifically TARP-27-35 and TARP-29-37-9V, could be used as a peptide vaccine in adjuvant or as peptide-pulsed DC in vaccine therapy for prostate and breast cancer patients who are positive for the HLA-A2 allele. Given that HLA-A2 is present in nearly half of the population of North America as well as much of the world, and that the expression of TARP is common in prostate and breast cancers, a vaccine containing or expressing these peptides can be effective in a sizable fraction of prostate and breast cancer patients. Such vaccine can also be used in combination with other antigens for prostate or breast cancer, such as PSA and PSMA, to enhance the efficacy of vaccine therapy. In addition, to enhance CD8+ T cell-mediated immune responses, recombinant vectors including adenovirus or vaccinia virus expressing those antigens can also be used.

It will be apparent that the precise details of the methods or compositions described may be varied or modified without departing from the spirit of the described invention. We claim all such modifications and variations that fall within the scope and spirit of the claims below.

The invention claimed is:

1. An isolated polypeptide consisting of SEQ ID NO: 6.
2. An immunogen comprising the polypeptide of claim 1, wherein the polypeptide is covalently linked to a carrier.
3. An isolated polynucleotide comprising a nucleic acid sequence encoding the polypeptide of claim 1.
4. The polynucleotide of claim 3, operably linked to a promoter.
5. An isolated vector comprising the polynucleotide of claim 4.
6. The isolated vector of claim 5, wherein the vector is a viral vector.
7. The isolated vector of claim 6, wherein the vector is a plasmid vector.
8. An isolated host cell transformed with the vector of claim 5.
9. A composition comprising an immunogenic amount of the polypeptide of claim 1 in a carrier.
10. A composition comprising an immunogenic amount of the polynucleotide of claim 3 in a carrier.
11. A reagent comprising a tetrameric MHC class I/peptide complex comprising the polypeptide of claim 1, wherein the reagent is labeled or unlabeled.
12. The reagent of claim 11, wherein the reagent is labeled.
13. The reagent of claim 11, wherein the label is a fluorochrome.
14. A method of detecting CD8 expressing T cells that specifically recognize a polypeptide comprising SEQ ID NO: 1 in a sample isolated from a subject, comprising contacting a sample containing peripheral blood mononuclear cells isolated from the subject with the reagent of claim 11; and detecting the presence of the reagent bound to the peripheral blood mononuclear cells, thereby detecting CD8 expressing T cells that specifically bind a polypeptide comprising SEQ ID NO: 1 in the sample.
15. The method of claim 14, wherein the subject has breast cancer.
16. The method of claim 14, wherein the subject has prostate cancer.
17. The method of claim 14, further comprising quantitating the number of CD8+ T cells that bind the reagent.
18. An isolated fusion polypeptide comprising the amino acid sequence of SEQ ID NO: 6 adjoined to the amino acid sequence of a heterologous polypeptide.
19. An isolated polynucleotide comprising a nucleic acid sequence encoding the polypeptide of claim 18.
20. The isolated polynucleotide of claim 19, operably linked to a promoter.
21. An isolated vector comprising the polynucleotide of claim 20.
22. The isolated vector of claim 21, wherein the vector is a viral vector.
23. The isolated vector of claim 21, wherein the vector is a plasmid vector.
24. An isolated host cell transformed with the vector of claim 21.
25. A composition comprising an immunogenic amount of the polypeptide of claim 18 in a carrier.

* * * * *